US009790271B2

(12) United States Patent
Zauderer et al.

(10) Patent No.: US 9,790,271 B2
(45) Date of Patent: Oct. 17, 2017

(54) METHODS FOR INCREASING IMMUNOGLOBULIN A LEVELS

(71) Applicant: Vaccinex, Inc., Rochester, NY (US)

(72) Inventors: Maurice Zauderer, Pittsford, NY (US); Masaru Yoshida, Hyogo (JP); Koji Yamamoto, Hokkaido (JP); Ernest S. Smith, Rochester, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 14/765,162

(22) PCT Filed: Jan. 31, 2014

(86) PCT No.: PCT/US2014/014107
§ 371 (c)(1),
(2) Date: Jul. 31, 2015

(87) PCT Pub. No.: WO2014/121053
PCT Pub. Date: Aug. 7, 2014

(65) Prior Publication Data
US 2015/0368332 A1    Dec. 24, 2015

Related U.S. Application Data

(60) Provisional application No. 61/759,108, filed on Jan. 31, 2013.

(51) Int. Cl.
A61K 39/395    (2006.01)
C07K 16/24     (2006.01)
A61K 39/00     (2006.01)

(52) U.S. Cl.
CPC ........ C07K 16/24 (2013.01); A61K 2039/505 (2013.01); A61K 2039/545 (2013.01); C07K 2317/56 (2013.01); C07K 2317/565 (2013.01); C07K 2317/76 (2013.01)

(58) Field of Classification Search
None
See application file for complete search history.

(56) References Cited

U.S. PATENT DOCUMENTS

| 5,633,149 | A | 5/1997 | Guegler et al. |
| 5,844,084 | A | 12/1998 | Guegler et al. |
| 6,071,701 | A | 6/2000 | Guegler et al. |
| 6,110,695 | A | 8/2000 | Gunn et al. |
| 6,692,920 | B1 | 2/2004 | Guegler et al. |
| 6,852,508 | B1 | 2/2005 | Herrmann et al. |
| 7,390,884 | B2 | 6/2008 | Segal et al. |
| 8,546,538 | B2 | 10/2013 | Segal et al. |
| 2002/0111290 | A1 | 8/2002 | Homey et al. |
| 2003/0017979 | A1 | 1/2003 | Mack et al. |
| 2003/0026802 | A1 | 2/2003 | Markovitz et al. |
| 2003/0027136 | A1 | 2/2003 | Goronzy et al. |
| 2003/0124628 | A1 | 7/2003 | Burns et al. |
| 2003/0186889 | A1 | 10/2003 | Forssmann et al. |
| 2004/0010124 | A1 | 1/2004 | Johnson et al. |
| 2004/0018563 | A1 | 1/2004 | Burns et al. |
| 2004/0170628 | A1 | 9/2004 | Lillard et al. |
| 2004/0191255 | A1 | 9/2004 | Lillard et al. |
| 2004/0214864 | A1 | 10/2004 | Cage et al. |
| 2005/0129695 | A1 | 6/2005 | Mercken et al. |
| 2006/0286556 | A1 | 12/2006 | Segal et al. |
| 2007/0004909 | A1 | 1/2007 | Johnson et al. |
| 2007/0048301 | A1 | 3/2007 | Bodary-Winter et al. |
| 2007/0136826 | A1 | 6/2007 | Dunn et al. |
| 2007/0185017 | A1 | 8/2007 | Aggarwal et al. |
| 2007/0190599 | A1 | 8/2007 | Nakano et al. |
| 2008/0181888 | A1 | 7/2008 | Ambrose et al. |
| 2008/0227704 | A1 | 9/2008 | Kamens |
| 2009/0041783 | A1 | 2/2009 | Takayama et al. |
| 2009/0286860 | A1 | 11/2009 | Nabel et al. |
| 2010/0086942 | A1 | 4/2010 | Barker et al. |
| 2014/0147447 | A1 | 5/2014 | Klimatcheva et al. |
| 2015/0125467 | A1 | 5/2015 | Smith et al. |
| 2016/0002325 | A1 | 1/2016 | Klimatcheva et al. |

FOREIGN PATENT DOCUMENTS

| CN | 101636413 A | 1/2010 |
| JP | 2009/534419 A | 9/2009 |
| JP | 2010-519280 A | 6/2010 |
| JP | 2010-523580 A | 7/2010 |
| WO | WO 93/14125 | 7/1993 |
| WO | WO 96/17868 | 6/1996 |
| WO | WO 96/39522 | 12/1996 |
| WO | WO 98/11226 | 3/1998 |

(Continued)

OTHER PUBLICATIONS

Paul, Fundamental Immunology, 3rd Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Piatesi et al ChemBio Chem 5: 460-466, 2004).*
Stancovski et al. Proceedings of the National Academy of Science USA 88: 8691-8695, 1991.*
Czinn et al. 1993. Vaccine 11:637-642.*
Aagaard, L. and Rossi, J.J., "RNAi therapeutics: principles, prospects and challenges," *Advanced Drug Delivery Reviews*, 2007, vol. 59, pp. 75-86.
Ajuebor, M.N., et al., "Chemokines as novel therapeutic targets in inflammatory diseases," *Biochem Pharmacol*, 2002, vol. 63, No. 7, pp. 1191-1196.
Alley, J. et al., "A human CXCL13-induced actin polymerization assay measured by fluorescence plate reader," *ASSAY and Drug Development Technologies*, 2010, vol. 8, No. 1, pp. 73-84.
Al-Mughales, J., et al., "The chemoattractant activity of rheumatoid synovial fluid for human lymphocytes is due to multiple cytokines," *Clin Exp Immunol*, 1996, vol. 106, pp. 230-236.
Aloisi, F. and Pufol-Borrell, R., "Lymphoid neogenesis in chronic inflammatory diseases," *Nat Rev Immunol*, 2006, vol. 6, No. 3, pp. 205-217.
Aloisi, F., et al., "Functional maturation of adult mouse resting microglia into an APC is promoted by granulocyte-macrophage colony-stimulating factor and interaction with Th1 cells," *J. Immunol.*, 2000, vol. 164, pp. 1705-1712.

(Continued)

*Primary Examiner* — Shulamith H Shafer
(74) *Attorney, Agent, or Firm* — Thompson Coburn LLP

(57) ABSTRACT

Methods for increasing immunoglobulin A (IgA) levels in a subject having a deficiency thereof are provided herein by administering to the subject an agent that inhibits CXCL13 activity, such as an anti-CXCL13 or an anti-CXCR5 antibody. Further provided are methods for treating an inflammatory disorder in a subject deficient for IgA by administering to the subject an agent that inhibits CXCL13 activity.

30 Claims, 6 Drawing Sheets

(56) References Cited

FOREIGN PATENT DOCUMENTS

| WO | WO 2007/122402 | 11/2007 |
|---|---|---|
| WO | WO 2008/079361 | 7/2008 |
| WO | WO 2008/102123 | 8/2008 |
| WO | WO 2008/121940 | 10/2008 |
| WO | WO 2010/053547 | 5/2010 |
| WO | WO 2012/031099 | 3/2012 |
| WO | WO 2012/031099 A2 | 3/2012 |
| WO | WO 2013/102123 | 7/2013 |
| WO | WO 2013/130959 | 9/2013 |
| WO | WO 2013/130959 A1 | 9/2013 |
| WO | WO 2014/137355 | 9/2014 |

OTHER PUBLICATIONS

Alt, C., et al., "Functional expression of the lymphoid chemokines CCL19 (ELC) and CCL 21 (SLC) at the blood-brain barrier suggests their involvement in G-protein-dependent lymphocyte recruitment into the central nervous system during experimental autoimmune encephalomyelitis," *Euro. J. Immunol.*, 2002, vol. 32, pp. 2133-2144.

Ando, D.G., et al., "Encephalitogenic T-cells in the B10.PL model of experimental allergic encephalomyelitis (EAE) are of the Th-1 lymphokine subtype" *Cell Immunol.*, 1989, vol. 124, pp. 132-143.

Ansel, K.M., et al., "A chemokine-driven positive feedback loop organizes lymphoid follicles," *Nature*, 2000, vol. 406, No. 6793, pp. 309-314.

Ansel, K.M., et al., "CXCL13 is Required for B1 Cell Homing, Natural Antibody Production, and Body Cavity Immunity," *Immunity*, 2002, vol. 16, No. 1, pp. 67-76.

Ansel, K.M., et al., "In Vivo-activated CD4 T Cells Upregulate CXC Chemokine Receptor 5 and Reprogram Their Response to Lymphoid Chemokines," *J Exp Med*, 1999, vol. 190, No. 8, pp. 1123-1134.

Armengol et al., "Chemokines Determine Local Lymphoneogenesis and a Reduction of Circulating CXCR4+ T and CCR7 B and T Lymphocytes in Thyroid Autoimmune Diseases," *J Immunol.* Jun. 15, 2003;170(12):6320-8.

Bachmann, M.F. and Kopf, M., "On the Role of the Innate Immunity in Autoimmune Disease," *J Exp Med*, 2001, vol. 193, No. 12, pp. F47-F50.

Bagaeva, L.V., et al., "CXC Chemokine Ligand 13 Plays a Role in Experimental Autoimmune Encephalomyelitis," *J Immunol*, 2006, vol. 176, No. 12, pp. 7676-7685.

Bagaeva, L.V., et al., "CXCL13 in the central nervous system (CNS) during experimental autoimmune encephalomyelitis," *FASEB J*, 2004, vol. 18, No. 5, p. A1134.

Bagaeva, L.V., et al., "IL-12 dependent/IFN gamma independent expression of CCR5 by myelin-reactive T cells correlates with encephalitogenicity," *J Neuroimmunol*, 2003, vol. 137, Nos. 1-2, pp. 109-116.

Bagaeva, L.V., et al., "Lymphoid chemokines in central nervous system (CNS) autoimmunity," 6th Ann Upstate New York Immunology Conference, Bolton Landing, NY, 2003, p. 36.

Baranzini, S.E., et al., "B-cell repertoire diversity and clonal expansion in multiple sclerosis brain lesions," *J. Immunol.*, 1999, vol. 163, pp. 5133-5144.

Baron, J.L., et al., "Surface expression of α4 integrin by CD4 T cells is required for their entry into brain parenchyma," *J. Exp. Med.*, 1993, vol. 177, pp. 57-68.

Barone, F., et al., "Association of CXCL13 and CCL21 Expression With the Progressive Organization of Lymphoid-like Structures in Sjögren's Syndrome," *Arthritis Rheum*, 2005, vol. 52, No. 6, pp. 1773-1784.

Barone, F., et al., "CXCL13, CCL21, and CXCL12 Expression in Salivary Glands of Patients with Sjögren's Syndrome and MALT Lymphoma: Association with Reactive and Malignant Areas of Lymphoid Organization," *J Immunol*, 2008, vol. 180, pp. 5130-5140.

Bauer, J., et al., "The role of macrophage subpopulations in autoimmune disease of the central nervous system" *Histochemical Journal*, 1996, vol. 28, pp. 83-97.

Bauer, J., et al., "The role of macrophages, perivascular cells, and microglial cells in the pathogenesis of experimental autoimmune encephalomyelitis" *Glia*, 1995, vol. 15, pp. 437-446.

Beagley, K.W., et al., "Interleukins and IgA synthesis: Human and murine interleukin 6 induce high rate IgA secretion in IgA-committed B cells," *J Exp Med*, 1989, vol. 169, pp. 2133-2148.

Becher, B., et al., "Experimental autoimmune encephalitis and inflammation in the absence of interleukin-12," *J. Clin. Invest.*, 2002, vol. 110, pp. 493-497.

Beeton, C., et al., "Kv1.3 channels are a therapeutic target for T cell-mediated autoimmune diseases," *Proc. Natl. Acad. Sci. U.S.A.*, 2006, vol. 103, pp. 17414-17419.

Biber. K., et al., "Ischemia-induced neuronal expression of the microglia attracting chemokine secondary lymphoid-tissue chemokine (SLC)" *Glia*, 2001, vol. 34, pp. 121-133.

Bielekova, B., et al., "Encephalitogenic potential of the myelin basic protein peptide (amino acids 83-99) in multiple sclerosis: results of a phase II clinical trial with an altered peptide ligand" *Nat. Med.*, 2000, vol. 6, pp. 1167-1175.

Bork, P., "Powers and pitfalls in sequence analysis: the 70% hurdle," *Genome Research*, 2000, vol. 10, pp. 398-400.

Boven, L.A., et al., "Macrophage inflammatory protein-1α (MIP-1α), MIP-1β, and RANTES mRNA semiquantification and protein expression in active demyelinating multiple sclerosis (MS) lesions," *Clin. Exp. Immunol.*, 2000, vol. 122, pp. 257-263.

Bowie, J.U., et al., "Deciphering the message in protein sequences: tolerance to amino acid substitutions," *Science*, 1990, vol. 247, pp. 1306-1310.

Brown, M., et al., "Tolerance to single, but not multiple, amino acid replacements in antibody $V_H$ CDR2," *J. Immunol*, 1996, vol. 156, pp. 3285-3291.

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 1990, vol. 111, pp. 2129-2138.

Bürkle, A., et al., "Overexpression of the CXCR5 chemokine receptor, and its ligand, CXCL13 in B-cell chronic lymphocytic leukemia," *Blood*, 2007, vol. 110, pp. 3316-3325.

Campbell, J.J., et al., "6-C-kine (SLC), a lymphocyte adhesion-triggering chemokine expressed by high endothelium, is an agonist for the MIP-3β receptor CCR7," *J. Cell Biol.*, 1998, vol. 141, pp. 1053-1059.

Cannella, B., et al., "Upregulation and Coexpression of Adhesion Molecules Correlate with Relapsing Autoimmune Demyelination in the Central Nervous System," *J Exp Med*, 1990, vol. 172, No. 5, pp. 1521-1524.

Carlsen, H.S., et al., "Monocyte-like and mature macrophages produce CXCL13 (B cell-attracting chemokine 1) in inflammatory lesions with lymphoid neogenesis," *Blood*, 2004, vol. 104, No. 10, pp. 3021-3027.

Casset, F., et al., "A peptide mimetic of an anti-CD4 monoclonal antibody by rational design," *Biochem Biophys Res Comm*, 2003, vol. 307, pp. 198-205.

Cella, M., et al., "Ligation of CD40 on dendritic cells triggers production of high levels of interleukin-12 and enhances T cell stimulatory capacity: T-T help via APC activation," *J. Exp. Med.*, 1996, vol. 184, pp. 747-752.

Chen, Y.,et al., "Selection and analysis of an optimized anti-VEGF antibody: crystal structure of an affinity-matured Fab in complex with antigen," J Mol. Biol., 1999, vol. 293, pp. 865-881.

Chen, S-C., et al., "Central nervous system inflammation and neurological disease in transgenic mice expressing the CC chemokine CCL21 in oligodendrocytes," *J. Immunol.*, 2002, vol. 168, No. 3, pp. 1009-1017.

Chen, X.Y., et al., "*Helicobacter pylori* associated gastric diseases and lymphoid tissue hyperplasia in gastric antral mucosa," *J Clin Pathol*, 2002, vol. 55, pp. 133-137.

(56) References Cited

OTHER PUBLICATIONS

Chintalacharuvu, S.R., et al., "Treatment of collagen induced arthritis by proteolytic enzymes: immunomodulatory and disease modifying effects," *Journal of Rheumatology*, 2001, vol. 28, pp. 2049-2059.
Clark, J.D., et al., "Discovery and development of janus kinase (JAK) inhibitors for inflammatory diseases," *J. Med. Chem.*, 2014, vol. 57, pp. 5023-5038.
Colombo, M., et al., "Accumulation of clonally related B lymphocytes in the cerebrospinal fluid of multiple sclerosis patients," *J. Immunol.*, 2000, vol. 164, pp. 2782-2789.
Columba-Cabezas, S., et al., "Lymphoid chemokines CCL19 and CCL21 are expressed in the central nervous system during experimental autoimmune encephalomyelitis: implications for the maintenance of chronic neuroinflammation" *Brain Pathology*, 2003, vol. 13, pp. 38-51.
Corcione, A., et al., "Recapitulation of B cell differentiation in the central nervous system of patients with multiple sclerosis," *Proc Natl Acad Sci USA*, 2004, vol. 101, No. 30, pp. 11064-11069.
Correale, J., et al., "Oligoclonal bands and antibody responses in multiple sclerosis" *J. of Neurology*, 2002, vol. 249, pp. 375-389.
Cote, R.J., et al., "Specificity analysis of human monoclonal antibodies reactive with cell surface and intracellular antigens," *Proc. Natl. Acad. Sci. U.S.A.*, 1986, vol. 83, pp. 2959-2963.
Cross, A.H., et al., "B cells and antibodies in CNS demyelinating disease" *J. Neuroimmunol.*, 2001, vol. 112, pp. 1-14.
Cross, A.H., et al., "Homing to central nervous system vasculature by antigen-specific lymphocytes. I. Localization of $^{14}C$-labeled cells during acute, chronic, and relapsing experimental allergic encephalomyelitis," *Lab. Invest.*, 1990, vol. 63, pp. 162-170.
Cyster, J.G., "Chemokines and Cell Migration in Secondary Lymphoid Organs," *Science*, 1999, vol. 286, No. 5447, pp. 2098-2102.
De Padilla, C.M.L., et al., Extranodal Lymphoid Microstructures in Inflamed Muscle and Disease Severity of New-Onset Juvenile Dermatomyositis, *Arthritis Rheu*, 2009, vol. 60, No. 4, pp. 1160-1172.
Delalande, S., et al., "Neurologic manifestations in primary Sjögren syndrome: a study of 82 patients," *Medicine* (Baltimore), 2004, vol. 83, pp. 280-291.
Dighiero, G., et al., "High frequency of natural autoantibodies in normal newborn mice," *J Immunol*, 1985, vol. 134, pp. 765-771.
Eugster, H-P., et al., "Severity of symptoms and demyelination in MOG-induced EAE depends on TNFR1," *Eur. J. Immunol.*, 1999, vol. 29, pp. 626-632.
Fan, L., et al., "Cutting edge: Ectopic expression of the chemokine TCA4/SLC is sufficient to trigger lymphoid neogenesis," *J. Immunol.*, 2000, vol. 164, No. 8, pp. 3955-3959.
Fava, R., et al., "Lymphotoxin-beta receptor blockade reduces CXCL13 in lacrimal glands and improves corneal integrity in the NOD model of Sjögren's syndrome," *Arthritis Research & Therapy*, 2011, vol. 13(6), pp. 1-20.
Fazilleau, N., et al., "Follicular helper T cells: Lineage and location," *Immunity*, 2009, vol. 30, pp. 324-335.
Fife, B.T., et al., "Selective CC chemokine receptor expression by central nervous system-infiltrating encephalitogenic T cells during experimental autoimmune encephalomyelitis," *J Neurosci Res*, 2001, vol. 66, No. 4, pp. 705-714.
Finke, D., et al., "CD4$^+$CD3$^-$ Cells Induce Peyer's Patch Development: Role of $\alpha 4\beta 1$ Integrin Activation by CXCR5," *Immunity*, 2002, vol. 17, pp. 363-373.
Fischer, H.-G. and Reichmann, G., "Brain Dendritic Cells and Macrophages/Microglia in Central Nervous System Inflammation," *J Immunol*, 2001, vol. 166, No. 4, pp. 2717-2726.
Förster, R., "CXCR5," Cytokine Reference: A compendium of cytokines and other mediators of host defense, Oppenheim, J.J. and Feldmann, M., eds., Academic Press, Aug. 2000, pp. 2019-2024.
Förster, R., et al., "A Putative Chemokine Receptor, BLR1, Directs B Cell Migration to Defined Lymphoid Organs and Specific Anatomic Compartments of the Spleen," *Cell*, 1996, vol. 87, No. 6, pp. 1037-1047.
Förster, R., et al., "Expression of the G-protein—coupled receptor BLR1 defines mature, recirculating B cells and a subset of T-helper memory cells," *Blood*, 1994, vol. 84, pp. 830-840.
Fox, R.I., "Sjögren's syndrome," *Lancet*, 2005, vol. 366, pp. 321-331.
Friese, M.A., et al., "The value of animal models for drug development in multiple sclerosis," *Brain*, 2006, vol. 129, No. 8, pp. 1940-1952.
García-Carrasco, M., et al., "Raynaud's phenomenon in primary Sjögren's syndrome. Prevalence and clinical characteristics in a series of 320 patients," *J Rheumatol*, 2002, vol. 29, pp. 726-730.
García-López, M.A., et al., "CXCR3 chemokine receptor distribution in normal and inflamed tissues: Expression on activated lymphocytes, endothelial cells, and dendritic cells," *Laboratory Investigation*, 2001, vol. 81, No. 3, pp. 409-418.
Genain, C.P., et al., "Antibody facilitation of multiple sclerosis-like lesions in a nonhuman primate," *Journal of Clinical Investigation*, 1995, vol. 96, pp. 2966-2974.
Genta, R.M., et al., "Gastric lymphoid follicles in *Helicobacter pylori* infection: frequency, distribution, and response to triple therapy," *Hum Pathol*, 1993, vol. 24, pp. 577-583.
Gerritse, K.., et al., "The involvement of specific anti myelin basic protein antibody-forming cells in multiple sclerosis immunopathology" *J. Neuroimmunol.*, 1994, vol. 49, pp. 153-159.
Giraudon, P., et al., "Semaphorin CD100 from Activated T Lymphocytes Induces Process Extension Collapse in Oligodendrocytes and Death of Immature Neural Cells," *J Immunol*, 2004, vol. 172, No. 2, pp. 1246-1255.
Gold, R., et al., "Understanding pathogenesis and therapy of multiple sclerosis via animal models: 70 years of merits and culprits in experimental autoimmune encephalomyelitis research," *Brain*, 2006, vol. 129, No. 8, pp. 1953-1971.
Gommerman, J.L., et al., "A role for surface lymphotoxin in experimental autoimmune encephalomyelitis independent of LIGHT," *J. Clin. Invest.*, 2003, vol. 112, pp. 755-767.
Gong, Q., et al., "Importance of Cellular Microenvironment and Circulatory Dynamics in B Cell Immunotherapy," *J Immunol*, 2005, vol. 174, No. 2, pp. 817-826.
Guido, R.V.C., et al., "Virtual screening and its integration with modern drug design technologies," *Curr Med Chem*, 2008, vol. 15, pp. 37-46.
Gunn, M.D., et al., "Mice lacking expression of secondary lymphoid organ chemokine have defects in lymphocyte homing and dendritic cell localization," *J. Exp. Med.*, 1999, vol. 189, pp. 451-460.
Gunn, M.D., et al., "A B-cell-homing chemokine made in lymphoid follicles activates Burkitt's lymphoma receptor-1," *Nature*, 1998, vol. 391, pp. 799-803.
Günther, K., et al., "Prediction of lymph node metastasis in colorectal carcinoma by expression of chemokine receptor CCR7," *Int J Cancer*, 2005, vol. 116, pp. 726-733.
Hamaguchi, Y., et al., "The Peritoneal Cavity Provides a Protective Niche for B1 and Conventional B Lymphocytes during Anti-CD20 Immunotherapy in Mice," *J Immunol*, 2005, vol. 174, pp. 4389-4399.
Haringman, J.J., et al., "Chemokines in joint disease: the key to inflammation?," *Ann Rheum Dis*, 2004, vol. 63, No. 10, pp. 1186-1194.
Haverkos, H.W., et al., "Enteroviruses and Type 1 diabetes mellitus," *Biomedicine and Pharmacotherapy*, 2003, vol. 57, pp. 379-385.
Hikino, H., et al., "GM-CSF-independent development of dendritic cells from bone marrow cells in the GM-CSF-receptor deficient mouse" *Trans. Proc.*, 2000, vol. 32, pp. 2458-2459.
Hjelmström, P., "Lymphoid neogenesis: de novo formation of lymphoid tissue in chronic inflammation through expression of homing chemokines," *J Leukocyte Bio*, 2001, vol. 69, No. 3, pp. 331-339.
Hjelmström, P., et al., "Lymphoid Tissue Homing Chemokines are Expressed in Chronic Inflammation," *Am J Pathol*, 2000, vol. 156, No. 4, pp. 1133-1138.

(56) References Cited

OTHER PUBLICATIONS

Honeyman, M., "How robust is the evidence for viruses in the induction of type 1 diabetes?," *Current Opinion of Immunology*, 2005, vol. 17, pp. 616-623.

Houshmand, P. and Zlotnik, A., "Therapeutic applications in the chemokine superfamily," *Curr Opin Chem Biol*, 2003, vol. 7, No. 4, pp. 457-460.

Hussain, R., et al., "Selective Increases in Antibody Isotypes and Immunoglobulin G Subclass Responses to Secreted Antigens in Tuberculosis Patients and Healthy Household Contacts of the Patients," *Clin Diag. Lab. Immunol.*, 1995, vol. 2, No. 6, pp. 726-732.

Husson, H., et al., "CXCL13 (BCA-1) is produced by follicular lymphoma cells: role in the accumulation of malignant B Cells," *Br J Haematol*, 2002, vol. 119, No. 2, pp. 492-495.

Iglesias, A., et al., "T- and B-cell responses to myelin oligodendrocyte glycoprotein in experimental autoimmune encephalomyelitis and multiple sclerosis" *Glia*, 2001, vol. 36, pp. 220-234.

Ishikawa, S., et al., "Aberrant High Expression of B Lymphocyte Chemokine (BLC/CXCL13) by C11b$^+$CD11c$^+$ Dendritic Cells in Murine Lupus and Preferential Chemotaxis of B1 Cells Towards BLC," *J Exp Med*, 2001, vol. 193, No. 12, pp. 1393-1402.

Itakura, M., et al., "Blockade of secondary lymphoid tissue chemokine exacerbates *Propionibacterium acnes*-induced acute lung inflammation," *J. Immunol.*, 2001, vol. 166, pp. 2071-2079.

Jenh, C.H., et al., "Human B cell-attracting chemokine 1 (BCA-1; CXCL13) is an agonist for the human CXCR3 receptor," *Cytokine*, 2001, vol. 15, No. 3, pp. 113-121.

Kanwar, J.R., et al., "B7 integrins contribute to demyelinating disease of the central nervous system" *J. Neuroimmunol.*, 2000, vol. 103, pp. 146-152.

Karpus, W.J. and Ransohoff, R.M., "Cutting Edge Commentary: Chemokine Regulation of Experimental Autoimmune Encephalomyelitis: Temporal and Spatial Expression Patterns Govern Disease Pathogenesis," *J Immunol*, 1998, vol. 161, No. 6, pp. 2667-2671.

Kawakami, N., et al., "The activation status of neuroantigen-specific T cells in the target organ determines the clinical outcome of autoimmune encephalomyelitis," *J. Exp. Med.*, 2004, vol. 199, pp. 185-197.

Kim, C.H., et al., "Subspecialization of CXCR5$^+$ T Cells: B Helper Activity is Focused in a Germinal Center-localized Subset of CXCR5$^+$ T Cells," *J Exp Med*, 2001, vol. 193, No. 12, pp. 1373-1381.

King, G.L., "The Role of Inflammatory Cytokines in Diabetes and Its Complications," *J Periodontol*, 2008, vol. 79, pp. 1527-1534.

Klimatcheva, E., et al., "CXCL13 antibody for the treatment of autoimmune disorders," *BMC Immunology*, 2015, vol. 16, No. 6, pp. 1-17.

Körner, H., et al., "Critical points of tumor necrosis factor action in central nervous system autoimmune inflammation defined by gene targeting" *J. Exp. Med.*. 1997, vol. 186, pp. 1585-1590.

Krumbholz, M., et al., "Chemokines in multiple sclerosis: CXCL12 and CXCL13 up-regulation is differentially linked to CNS immune cell recruitment," *Brain*, 2006, vol. 129, pp. 200-211.

Kumanogoh, A., et al., "Requirement for the lymphocyte semaphorin, CD100, in the induction of antigen-specific T cells and the maturation of dendritic cells," J Immunol, 2002, vol. 169, pp. 1175-1181.

Lammi, N., et al., "Do microbes have a causal role in type 1 diabetes?," *Medical Science Monitor*, 2005, vol. 11, No. 3, pp. RA63-RA69.

Lamminmaki, U., et al., "Crystal structure of a recombinant anti-estradiol Fab fragment in complex with 17β-estradiol," J. Biol. Chem., 2001, vol. 276, No. 39, pp. 36687-36694.

Lazar, E., et al., "Transforming growth factor α: mutation of aspartic acid 47 and leucine 48 results in different biological activities," *Mol Cell Biol*, 1988, vol. 8, pp. 1247-1252.

Lee, H.T., et al., "Serum BLC/CXCL13 concentrations and renal expression of CXCL13/CXCR5 in patients with systemic lupus erythematosus and lupus nephritis," *J Rheum*, 2010, vol. 37, pp. 45-52.

Legler, D.F., et al., "B cell-attracting chemokine 1, a human CXC chemokine expressed in lymphoid tissues, selectively attracts B lymphocytes via BLR1/CXCR5," *J. Exp. Med.*, 1998, vol. 187, pp. 655-660.

Lim, H.W., et al., "Regulatory T cells can migrate to follicles upon T cell activation and suppress GC-Th cells and GC-Th cell-driven B cell responses," *J Clin Invest*, 2004, vol. 114, pp. 1640-1649.

Loetscher, P. and Moser, B., "Homing chemokines in rheumatoid arthritis," *Arthritis Research*, 2002, vol. 4, pp. 233-236.

Ludewig, B., et al., "Dendritic Cells Induce Autoimmune Diabetes and Maintain Disease via De Novo Formation of Local Lymphoid Tissue," *J Exp Med*, 1998, vol. 188, No. 8, pp. 1493-1501.

Luther, S.A., et al., "BLC expression in pancreatic islets causes B cell recruitment and lymphotoxin-dependent lymphoid neogenesis," *Immunity*, 2000, vol. 12, pp. 471-481.

Luther, S.A., et al., "Coexpression of the chemokines ELC and SLC by T zone stromal cells and deletion of the ELC gene in the *plt/plt* mouse," *Proc. Natl. Acad. Sci. U.S.A.*, 2000, vol. 97, pp. 12694-12699.

Luther, S.A., et al., "Differing activities of homeostatic chemokines CCL19, CCL21 and CXCL12 in lymphocyte and dendritic cell recruitment and lymphoid neogenesis," *J. Immunol.*, 2002, vol. 169, pp. 424-433.

Luther, S.A., et al., "Overlapping roles of CXCL13, interleukin 7 receptor α, and CCR7 ligands in lymph node development," *J. Exp. Med.*, 2003, vol. 197, pp. 1191-1198.

Lyons, J.-A., et al., "B cells are critical to induction of experimental allergic encephalomyelitis by protein but not by a short encephalitogenic peptide" *European J. Immunol.*, 1999, vol. 29, pp. 3432-3439.

Lyons, J.-A., et al., "Critical role of antigen-specific antibody in experimental autoimmune encephalomyelitis induced by recombinant myelin oligodendrocyte glycoprotein," *Eur. J. Immunol.*, 2002, vol. 32, pp. 1905-1913.

MAb 470 product data sheet, "Mouse CXCL13/BLC/BCA-1 Antibody," Monoclonal Rat IgG2A, Clone # 143614, Catalog No. MAB470, R&D Systems, Sep. 13, 2010, pp. 1-2.

MAb 4701 product data sheet, Mouse CXCL13/BLC/BCA-1 Antibody, R&D Systems, Monoclonal Rat IgG2A Clone # 143608, Catalog No. MAB4701, R&D Systems, Nov. 15, 2010, pp. 1-2.

MAb 801 product data sheet, "Human CXCL13/BLC/BCA-1 Antibody," Monoclonal Mouse IgG1, Clone # 53610, Catalog No. MAB801, R&D Systems, Oct. 7, 2010, pp. 1-2.

MacCallum, R.M., et al., "Antibody-antigen interactions: contact analysis and binding site topography," J. Mol. Biol., 1996, vol. 262, pp. 732-745.

Magliozzi, R., et al., "Intracerebral expression of CXCL13 and BAFF is accompanied by formation of lymphoid follicle-like structures in the meninges of mice with relapsing experimental autoimmune encephalomyelities" *Journal of Neuroimmunology*, 2004, vol. 148, pp. 11-23.

Magliozzi, R., et al., "Meningeal B-cell follicles in secondary progressive multiple sclerosis associate with early onset of disease and severe cortical pathology," *Brain*, 2007, vol. 130, pp. 1089-1104.

Manzo, A., et al., "Systematic microanatomical analysis of CXCL13 and CCL21 in situ production and progressive lymphoid organization in rheumatoid synovitis," *Eur J Immunol*, 2005, vol. 35, pp. 1347-1359.

Manzo, A., et al., "Mature Antigen-Experienced T Helper Cells Synthesize and Secrete the B Cell Chemoattractant CXCL13 in the Inflammatory Environment of the Rheumatoid Joint," *Arthritis Rheu*, 2008, vol. 58, No. 11, pp. 3377-3387.

Marusic, S., et al., "Local delivery of granulocyte macrophage colony-stimulating factor by retrovirally transduced antigen-specific T cells leads to severe, chronic experimental autoimmune encephalomyelitis in mice" *Neuroscience Lett.*, 2002, vol. 332 pp. 185-189.

(56) References Cited

OTHER PUBLICATIONS

Matsumoto, Y., et al., "CDR3 Spectratyping Analysis of the TCR Repertoire in Myasthenia Gravis," *J Immunol*, 2006, vol. 176, pp. 5100-5107.
Mazzucchelli, L., et al., "BCA-1 is highly expressed in *Helicobacter pylori*-induced mucosa-associated lymphoid tissue and gastric lymphoma," *J Clin Invest*, 1999, vol. 104, pp. R49-R54.
McKeague and Derosa, "Challenges and opportunities for small molecule aptamer development," *J Nucl Acids*, 2012, vol. 2012, pp. 1-20.
McQualter, J.L., et al., "Granulocyte macrophage colony-stimulating factor: A new putative therapeutic target in multiple sclerosis," *J. Exp. Med.*, 2001, vol. 194, No. 7, pp. 873-881.
Meijer, J., et al., "The CXCR5 Chemokine Receptor is Expressed by Carcinoma Cells and Promotes Growth of Colon Carcinoma in the Liver," *Cancer Res*, 2006, vol. 66, No. 19, pp. 9576-9582.
Meraouna, A., et al., "The chemokine CXCL13 is a key molecule in autoimmune myasthenia gravis," *Blood*, 2006, vol. 108, No. 2, pp. 432-440.
Mori, S., et al., "Mice lacking expression of the chemokines CCL21-Ser and CCL19 (*plt* mice) demonstrate delayed but enhanced T cell immune responses," *J. Exp. Med.*, 2001, vol. 193, pp. 207-217.
Moscatiello et al., "Diabetes and liver disease: An ominous association," *Nutrition, Metabolism and Cardiovascular Diseases*, 2007, vol. 17, pp. 63-70.
Moser, B. and Loetscher, P., "Lymphocyte traffic control by chemokines" *Nature Immunology*, 2001, vol. 2, No. 2, pp. 123-128.
Nakano, H. and Gunn, M.D., "Gene duplications at the chemokine locus on mouse chromosome 4: Multiple strain-specific haplotypes and the deletion of secondary lymphoid-organ chemokine and EBI-1 ligand chemokine genes in the plt mutation," J. Immunol., 2001, vol. 166, No. 1, pp. 361-369.
Nedrud, J.G. and Lamm, M.E., "Adjuvants and the Mucosal Immune System," Topics in Vaccine Adjuvant Research (Spiggs, D.R., Koff, W.C., Eds.) CRC Press, Boca Raton, Fla. (1990).
Neel, N.F., et al., "Chemokine receptor internalization and intracellular trafficking," Cytokine Growth Factor Rev, 2005, vol. 16, pp. 637-658.
Ngo, V.N., et al., "Lymphotoxin α/β and tumor necrosis factor are required for stromal cell expression of homing chemokines in B and T cell areas of the spleen," J. Exp. Med., 1999, vol. 189, pp. 403-412.
Nobutani, K., et al., "Helicobacter heilmannii can induce gastric lymphoid follicles in mice via a Peyer's patch-independent pathway," FEMS Immunol Med Microbiol, 2010, vol. 60, pp. 156-164.
Notarangelo, L.D., et al., "Primary immunodeficiencies: 2009 update: The International Union of Immunological Societies (IUIS) Primary Immunodeficiencies (PID) Expert Committee," *J Allergy Clin Immunol*, 2009, vol. 124, pp. 1161-1178.
Okiyama, Y., et al., "*Helicobacter heilmannii* infection: Clinical, endoscopic and histopathological features in Japanese patients," *Pathol Int*, 2005, vol. 55, pp. 398-404.
Olschowka, J.A., et al., "Helper-free HSV-1 amplicons elicit a markedly less robust innate immune response in the CNS," *Mol. Therapy*, 2003, vol. 7, No. 2, pp. 218-227.
Oppenheim, J., et al., "Autoantigens act as tissue-specific chemoattractants," *Journal of Leukocyte Biology*, 2005, vol. 77, pp. 854-861.
Oppmann, B., et al., "Novel p19 protein engages IL-12p40 to form a cytokine, IL-23, with biological activities similar as well as distinct from IL-12," *Immunity*, 2000, vol. 13, pp. 715-725.
Padlan, E.A., et al., "Structure of an antibody-antigen complex: crystal structure of the HyHEL-10 Fab-lysozyme complex," Proc. Natl. Acad. Sci USA, 1989, vol. 86, pp. 5938-5942.
Panse, J., et al., "Chemokine CXCL13 is overexpressed in the tumour tissue and in the peripheral blood of breast cancer patients," *Br J Cancer*, 2008, vol. 99, pp. 930-938.
Pascalis, R.D., et al., "Grafting of 'abbreviated' complementarity-determining regions containing specifcity-determining residues essential for ligand contact to engineer a less immunogenic humanized monoclonal antibody," J Immunol, 2002, vol. 169, pp. 3076-3084.
Pashenkov, M., et al., "Inflammation in the central nervous system: the role for dendritic cells" *Brain Pathology*, 2003, vol. 12, pp. 23-33.
Pashenkov, M., et al., "Secondary lymphoid organ chemokines are elevated in the cerebrospinal fluid during central nervous system inflammation" *J. Neuroimmunol.*, 2003, vol. 135, pp. 154-160.
Paterson, P.Y. and Swanborg, R.H., "Demyelinating diseases of the central and peripheral nervous systems" In: Immunological Diseases; Samter, ed., pp. 1877-1916, Little, Brown and Company, Boston, MA (1998).
Petersen, L.D., et al., "Autoreactive and immunoregulatory T-cell subsets in insulin-dependent diabetes mellitus," *Diabetologia*, 1999, vol. 42, pp. 443-449.
Prineas, J.W., "Multiple sclerosis: Presence of lymphatic capillaries and lymphoid tissue in the brain and spinal cord" *Science*, 1979, vol. 203, pp. 1123-1125.
Prineas, J.W., et al., "Macrophages, lymphocytes, and plasma cells in the perivascular compartment in chronic multiple sclerosis" *Lab. Invest.*, 1978, vol. 38, pp. 409-421.
Raine, C.S., et al., "Adhesion molecules on endothelial cells in the central nervous system: An emerging area in the neuroimmunology of multiple sclerosis" *Clinical Immunology & Immunopathology*, 1990, vol. 57, pp. 173-187.
Raine, C.S., et al., "Adoptively transferred chronic relapsing experimental autoimmune encephalomyelitis in the mouse" *Lab. Invest.*, 1984, vol. 51, pp. 534-546.
Raine, C.S., et al., "Homing to central nervous system vasculature by antigen-specific lymphocytes. II. Lymphocyte/endothelial cell adhesion during the initial stages of autoimmune demyelination" *Lab. Invest.*, 1990, vol. 63, pp. 476-489.
Raine, C.S., et al., "Neuropathology of experimental allergic encephalomyelitis in inbred strains of mice" *Lab. Invest.*, 1980, vol. 43, pp. 150-157.
Ramos-Casals, M., et al., "Primary Sjögren syndrome," *Medicine* (Baltimore), 2002, vol. 81, pp. 281-292.
Rioja, I., et al., "Potential Novel Biomarkers of Disease Activity in Rheumatoid Arthritis Patients: CXCL13, CCL23, Transforming Growth Factor α, Tumor Necrosis Factor Receptor Superfamily Member 9, and Macrophage Colony-Stimulating Factor," *Arthritis Rheu*, 2008, vol. 58, No. 8, pp. 2257-2267.
Rudikoff, S., et al., "Single amino acid substitution altering antigen-binding specificity," Proc Natl Acad Sci USA, 1982, vol. 79, pp. 1979-1983.
Saito, R., et al., "Altered expression of chemokine receptor CXCR5 on T cells of myasthenia gravis patients," *J Neuroimmunol*, 2005, vol. 170, Nos. 1-2, pp. 172-178.
Salomonsson, S., et al., "Expression of the B cell-attracting chemokine CXCL13 in the target organ and autoantibody production in ectopic lymphoid tissue in the chronic inflammatory disease Sjogren's syndrome," *Scan. J. Immunol.*, 2002, vol. 55, pp. 336-342.
Sansonno, D., et al., "Increased serum levels of the chemokine CXCL13 and up-regulation of its gene expression are distinctive features of HCV-related cryoglobulinemia and correlate with active cutaneous vasculitis," *Blood*, 2008, vol. 112, No. 5, pp. 1620-1627.
Santambrogio, L., et al., "Developmental plasticity of CNS microglia," *Proc. Natl. Acad. Sci. U.S.A.*, 2001, vol. 98, pp. 6295-6300.
Schiffer, L., et al., "Activated renal macrophages are markers of disease onset and disease remission in lupus nephritis," *J Immunol*, 2008, vol. 180, pp. 1938-1947.
Schiffer, L., et al., "B-cell-attracting chemokine CXCL13 as a marker of disease activity and renal involvement in systemic lupus erythematosus (SLE)," *Nephrol Dial Transplant*, 2009, vol. 24, No. 12, pp. 3708-3712.
Schiffer, L., et al., "Short Term Administration of Costimulatory Blockade and Cyclophosphamide Induces Remission of Systemic Lupus Erythematosus Nephritis in NZB/W $F_1$ Mice by a Mechanism Downstream of Renal Immune Complex Deposition," *J Immunol*, 2003, vol. 171, pp. 489-497.

(56) References Cited

OTHER PUBLICATIONS

Schmutz, C., et al., "Chemokine receptors in the rheumatoid synovium: upregulation of CXCR5," *Arthritis Res Ther*, 2005, vol. 7, No. 2, pp. R217-R229.
Segal, B.M. and Shevach, E.M., "IL-12 unmasks latent autoimmune disease in resistant mice," *J. Exp. Med.*, 1996, vol. 184, pp. 771-775.
Segal, B.M., et al.,"An interleukin (IL-)-10/IL-12 immunoregulatory circuit controls susceptibility to autoimmune disease," *J. Exp. Med.*, 1998, vol. 187, pp. 537-546.
Segal, B.M., et al., "CpG oligonucleotides are potent adjuvants for the activation of autoreactive encephalitogenic T cells in vivo," *J. Immunol.*, 2000, vol. 164, pp. 5683-5688.
Selmaj, K., et al., "Identification of lymphotoxin and tumor necrosis factor in multiple sclerosis lesions," *J. Clin. Invest.*, 1991, vol. 87, pp. 949-954.
Selmaj, K., et al., "Prevention of chronic relapsing experimental autoimmune encephalomyelitis by soluble tumor necrosis factor receptor I" *J Neuroimmunol.*, 1995, vol. 56, pp. 135-141.
Selmaj, K., et al.,"Suppression of experimental autoimmune encephalomyelitis with a TNF binding protein (TNFbp) correlates with down-regulation of VCAM-1/VLA-4," *Eur. J. Immunol.*, 1998, vol. 28, pp. 2035-2044.
Serafini, B., et al., "Detection of ectopic B-cell follicles with germinal centers in the meninges of patients with secondary progressive multiple sclerosis" *Brain Pathol.*, 2004, vol. 14, pp. 164-174.
Serafini, B., et al., "Intracerebral recruitment and maturation of dendritic cells in the onset and progression of experimental autoimmune encephalomyelitis," *American Journal of Pathology*, 2000, vol. 157, pp. 1991-2002.
Shi, K., et al., "Lymphoid chemokine B cell-attracting chemokine-1 (CXCL13) is expressed in germinal center of ectopic lymphoid follicles within the synovium of chronic arthritis patients," *J. Immunol.*, 2001, vol. 166, pp. 650-655.
Shi, W., et al., "The Class IV Semaphorin CD100 Plays Nonredundant Roles in the Immune System: Defective B and T Cell Activation in CD100-Deficient Mice," *Immunity*, 2000, vol. 13, pp. 633-642.
Shu, U., et al., "Activated T cells induce interleukin-12 production by monocytes via CD4O-CD40 ligand interaction," *Eur. J. Immunol.*, 1995, vol. 25, pp. 1125-1128.
Simpson, J.E., et al., "Expression of monocyte chemoattractant protein-1 and other β-chemokines by resident glia and inflammatory cells in multiple sclerosis lesions" *J. Neuroimmunol.*, 1998, vol. 84, pp. 238-249.
Singh, S., et al., "Serum CXCL13 positively correlates with prostatic disease, prostate-specific antigen and mediates prostate cancer cell invasion, integrin clustering and cell adhesion," *Cancer Letters*, 2009, vol. 283, No. 1, pp. 29-35.
Skundric, D.S., et al., "Experimental allergic encephalomyelitis: T-cell trafficking to the central nervous system in a resistant Thy-1 congenic mouse strain" *Lab. Invest.*, 1994, vol. 71, pp. 671-679.
Skundric, D.S., et al., "Homing of T cells to the central nervous system throughout the course of relapsing experimental autoimmune encephalomyelitis in Thy-1 congenic mice" *J. Neuroimmunol.*, 1993, vol. 46, pp. 113-121.
Smedby, K.E., et al., "Autoimmune disorders and risk of non-Hodgkin lymphoma subtypes: a pooled analysis within the InterLymph Consortium," *Blood*, 2008, vol. 111, pp. 4029-4038.
Smith, J.R., et al., "Expression of B-cell-attracting chemokine 1 (CXCL13) by malignant lymphocytes and vascular endothelium in primary central nervous system lymphoma," *Blood*, 2003, vol. 101, No. 3, pp. 815-821.
Sonoda, E., et al., "Transforming growth factor β induces IgA production and acts additively with interleukin 5 for IgA production," *J Exp Med*, 1989, vol. 170, pp. 1415-1420.
Spahn, T.W., et al., "Decreased severity of myelin oligodendrocyte glycoprotein peptide 33-35-induced experimental autoimmune encephalomyelitis in mice with a disrupted TCR δ chain gene," *Eur. J. Immunol.*, 1999, vol. 29, No. 12, pp. 4060-4071.

Stannard, C.J., et al., "Neutralization of CXCL13 Impacts B-cell Trafficking and Reduces Severity of Established Experimental Arthritis," Presented at American College of Rheumatology 2008 Annual Scientific Meeting, p. 1.
Steinmetz, O.M., et al., "Analysis and classification of B-cell infiltrates in lupus and ANCA-associated nephritis," *Kidney Int.*, 2008, vol. 74, pp. 448-457.
Steinmetz, O.M., et al., "BCA-1/CXCL13 expression is associated with CXCR5-positive B-cell cluster formation in acute renal transplant rejection," *Kidney Int*, 2005, vol. 67, No. 4, pp. 1616-1621.
Suarez-Pinzon, W.L. and Rabinovitch, A., "Approaches to Type 1 Diabetes Prevention by Intervention in Cytokine Immunoregulatory Circuits," *Int J Exp Diabetes Res*, 2001, vol. 2, No. 1, pp. 3-17.
Suen, W.E., et al., "A critical role for lymphotoxin in experimental allergic encephalomyelitis," *J. Exp. Med.*, 1997, vol. 186, pp. 1233-1240.
Suter, T., et al., "Dendritic cells and differential usage of the MHC class II transactivator promoters in the central nervous system in experimental autoimmune encephalitis," *Eur. J. Immunol.*, 2000, vol. 30, pp. 794-802.
Suzuki, K., and S. Fagarasan, "Diverse regulatory pathways for IgA synthesis in the gut," *Mucosal Immunology*, Nov. 2009, vol. 2, No. 6, pp. 468-471.
Takemura, S., et al., "Lymphoid neogenesis in rheumatoid synovitis," *J. Immunol.*, 2001, vol. 167, No. 2, pp. 1072-1080.
Theise, N.D., et al., "Radiation pneumonitis in mice: A severe injury model for pneumocyte engraftment from bone marros" *Exp. Hematol.*, 2002, vol. 30, pp. 1333-1338.
Traugott et al., "Autoimmune encephalomyelitis: Simultaneous identification of T and B cells in the target organ" *Science*, 1981, vol. 214, pp. 1251-1253.
Traugott et al., "Multiple Sclerosis: Distribution of T cells, T cell subsets and Ia-positive macrophages in lesions of different ages" *J Neuroimmunol.*, 1983, vol. 4, pp. 201-221.
Trentin, L., et al., "Homeostatic chemokines drive migration of malignant B cells in patients with non-Hodgkin lymphomas," *Blood*, 2004, vol. 104, No. 2, pp. 502-508.
Tumanov, A.V., et al., "Distinct role of surface lymphotoxin expressed by B cells in the organization of secondary lymphoid tissues," *Immunity*, 2002, vol. 17, pp. 239-250.
Ulvestad, E., et al., "Human microglial cells have phenotypic and functional characteristics in common with both macrophages and dendritic antigen-presenting cells," *J. Leukoc. Biol.*, 1994, vol. 56, pp. 732-740.
Unkeless, J.C., et al., "Structure and function of human and murine receptors for IgG," *Ann. Rev. Immunol.*, 1988, vol. 6, pp. 251-281.
Vajdos, F.F., et al., "Comprehensive functional maps of the antigen-binding site of an anti-ErbB2 antibody obtained with shotgun scanning mutagenesis," *J. Mol. Biol.*, 2002, vol. 320, pp. 415-428.
Vanderlugt, C.L., et al., "Pathologic role and temporal appearance of newly emerging autoepitopes in relapsing experimental autoimmune encephalomyelitis," *J. Immunol.*, 2000, vol. 164, pp. 670-678.
Vinuesa, C.G., et al., "Dysregulation of germinal centres in autoimmune disease," *Nat Rev Immunol*, 2009, vol. 9, pp. 845-857.
Vissers, J.L.M., et al., "BLC (CXCL13) is expressed by different dendritic cell subsets in vitro and in vivo," *Eur. J. Immunol.*, 2001, vol. 31, pp. 1544-1549.
Voskuhl, R.R., et al., "T helper 1 (TH1) functional phenotype of human myelin basic protein-specific T lymphocytes," *Autoimmunity*, 1993, vol. 15, pp. 137-143.
Voulgarelis, M., et al., "Malignant lymphoma in primary Sjögren's syndrome," *Arthr Rheum*, 1999, vol. 42, pp. 1765-1772.
Wang, N., et al., "Selective IgA Deficiency in Autoimmune Diseases," *Mol Med.*, 2011, vol. 17, Nos. 11-12, pp. 1383-1396.
Wang, X., et al., "Functional soluble CD100/Sema4D released from activated lymphocytes: possible role in normal and pathologic immune responses," *Blood*, 2001, vol. 97, pp. 3498-3504.
Warzocha, K. and Wotowiec D., "Antisense strategy: Biological utility and prospects in the treatment of hematological malignancies," *Leukemia and Lymphoma*, 1997, vol. 24, pp. 267-281.
Watanabe, C., et al., "Enhanced Immune Responses in Transgenic Mice Expressing a Truncated Form of the Lymphocyte Semaphorin CD100," *J Immunol*, 2001, vol. 167, No. 8, pp. 4321-4328.

(56) References Cited

OTHER PUBLICATIONS

Weyand, C.M., et al., "Ectopic lymphoid organogenesis: a fast track for autoimmunity," *American Journal of Pathology*, 2001, vol. 159, No. 3, pp. 787-793.

Wong, R.L., et al., "Murine T helper cell clones secrete granulocyte-macrophage colony-stimulating factor (GmCSF) by both interleukin-2-dependent and interleukin-2-independent pathways" *Cell. Immunol.*, 1989, vol. 123, pp. 445-455.

Wu, H., et al., "Humanization of a murine monoclonal antibody by simultaneous optimization of framework and CDR residues," J Mol Bio, 1999, vol. 294, pp. 151-162.

Wu, Q., et al., "Reversal of Spontaneous Autoimmune Insulitis in Nonobese Diabetic Mice by Soluble Lymphotoxin Receptor," *J Exp Med*, 2001, vol. 193, No. 11, pp. 1327-1332.

Yamamoto, K., et al., "Anti-CXCL13 antibody can inhibit the formation of gastric lymphoid follicles induced by *Helicobacter* infection," *Mucosal Immunology*, 2014, vol. 7, No. 5, pp. 1244-1254.

Yoneyama, H., et al., "Regulation by chemokines of circulating dendritic cell precursors, and the formation of portal tract-associated lymphoid tissue, in a granulomatous liver disease," *J. Exp. Med.*, 2001, vol. 193, pp. 35-49.

Yoon, J.-W. and Jun, H.-S., "Viruses cause type 1 diabetes in animals," *Annals New York Academy of Sciences*, 2006, vol. 1079, pp. 138-146.

Zheng, B., et al.,"CXCL13 neutralization reduces the severity of collagen-induced arthritis," *Arthr. Rheum.*, 2005, vol. 52, pp. 620-626.

Suzuki, K., and S. Fagarasan, "Diverse regulatory pathways for IgA synthesis in the gut," *Mucosal Immunology*, Nov. 2009, pp. 468-471, vol. 2(6).

Yamamoto, K., et al., "Anti-CXCL13 antibody can inhibit the formation of gastric lymphoid follicles induced by *Helicobacter* infection," *Mucosal Immunology*, Mar. 19, 2014, pp. 1-11.

\* cited by examiner

\* P<0.05
\*\* P<0.01

METHODS FOR INCREASING IMMUNOGLOBULIN A LEVELS

CROSS REFERENCE TO CORRESPONDING APPLICATIONS

This is a national stage application of PCT/US2014/014107 filed on Jan. 31, 2014, which claims priority from U.S. Provisional Application No. 61/759,108 filed on Jan. 31, 2013, which is incorporated herein by reference in its entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 441418SEQLIST.TXT, created on Jan. 20, 2014, and having a size of 35.3 kilobytes and is filed concurrently with the specification. The sequence listing contained in this ASCII formatted document is part of the specification and is herein incorporated by reference in its entirety.

FIELD OF THE INVENTION

The present invention relates generally to increasing immunoglobulin A (IgA) levels in a subject having a deficiency thereof.

BACKGROUND OF THE INVENTION

Immunoglobulins are a group of structurally related proteins composed of heavy and light chains comprised of variable and constant domains. The variable regions of the heavy and light chains determine the molecular specificity of the complete molecule. Immunoglobulins are categorized as IgG, IgM, IgE, IgD, or IgA based on the identity of the constant regions of their heavy chains Immunoglobulin A (IgA) comprises an alpha (a) constant region in its heavy chains.

IgA is produced by plasma cells located along the mucosal linings of the respiratory, gastrointestinal, and genitourinary tracts. IgA molecules bind to invading pathogens and weaken their ability to penetrate the mucosal layer and to enter the inner tissue and blood stream of the host. See generally J. G. Nedrud et al., "Adjuvants and the Mucosal Immune System", Topics in Vaccine Adjuvant Research, (Spiggs, D. E., Koff, W. C., Eds.) CRC Press, Boca Raton, Fla. (1990). IgA binds to receptors on the cell surface of phagocytic leukocytes and thereby facilitates antibody-dependent cell-mediated killing of invading pathogens. IgA can also bind allergenic substances, thereby preventing the allergens from binding IgE or activating T cells responsible for delayed-type hypersensitivity.

A deficiency of IgA can occur transiently, for example upon exposure to certain drugs or in response to various infections, or permanently, as in patients with congenital IgA deficiency.

It has been found that individuals with low IgA production are more prone to various inflammatory diseases, such as autoimmune diseases and allergies, than those with normal IgA levels. Thus, increasing the levels of either total IgA or antigen-specific IgA may treat or prevent inflammatory diseases.

BRIEF SUMMARY OF THE INVENTION

Methods for increasing immunoglobulin A (IgA) levels in a subject having a deficiency thereof are provided herein by administering an agent that inhibits CXCL13 activity, such as an anti-CXCL13 antibody. Further provided are methods for treating an inflammatory disorder in a subject deficient for IgA by administering to the subject an agent that inhibits CXCL13 activity. The IgA deficiency may be a permanent deficiency that is genetically determined or may be secondary to an infection or exposure to a drug. The administration of the CXCL13 inhibitory agent can prevent the development of an inflammatory disorder, such as an autoimmune disorder, or can treat an active inflammatory disorder.

The following embodiments are encompassed by the present invention.

1. A method for increasing immunoglobulin A (IgA) levels in a subject having a deficiency thereof, said method comprising administering to said subject an effective amount of an agent that inhibits CXCL13 activity.

2. The method of embodiment 1, wherein said IgA deficiency is secondary to an infection or exposure to a drug.

3. The method of embodiment 2, wherein said infection is a mucosal infection.

4. The method of embodiment 2 or 3, wherein said infection is a bacterial infection.

5. The method of embodiment 4, wherein said bacterial infection is a *Heliobacter* infection.

6. The method of embodiment 5, wherein said *Heliobacter* is selected from the group consisting of *Heliobacter pylori, Heliobacter heilmannii*, and *Heliobacter suis*.

7. The method of embodiment 6, wherein said *Heliobacter* is *H. suis*.

8. The method of embodiment 1, wherein said IgA deficiency is a primary IgA deficiency.

9. A method for treating an inflammatory disorder in a subject having an immunoglobulin A (IgA) deficiency, comprising administering to said subject an effective amount of an agent that inhibits CXCL13 activity.

10. The method of embodiment 9, wherein said inflammatory disorder is caused by a mucosal infection.

11. The method of embodiment 9 or 10, wherein said inflammatory disorder is caused by a bacterial infection.

12. The method of embodiment 11, wherein said method reduces the burden of said bacterial infection in said subject.

13. The method of embodiment 11 or 12, wherein said bacterial infection is a *Heliobacter* infection.

14. The method of embodiment 13, wherein said *Heliobacter* is selected from the group consisting of *Heliobacter pylori, Heliobacter heilmannii*, and *Heliobacter suis*.

15. The method of embodiment 14, wherein said *Heliobacter* is *H. suis*.

16. The method of any one of embodiments 10-15, wherein said mucosal infection is a gastric mucosal infection.

17. The method of any one of embodiments 9-16, wherein said inflammatory disorder is MALT lymphoma.

18. The method of embodiment 17, wherein said MALT lymphoma is a gastric MALT lymphoma.

19. The method of any one of embodiments 9-16, wherein said inflammatory disorder is a gastric or duodenal ulcer.

20. The method of embodiment 9, wherein said inflammatory disorder is an autoimmune disorder.

21. The method of embodiment 20, wherein said autoimmune disorder is selected from the group consisting of rheumatoid arthritis, systemic lupus erythematosus, Graves disease, Type 1 diabetes, myasthenia gravis, and celiac sprue.

22. The method of any one of embodiments 1-21, wherein secretory IgA levels are increased in said subject upon administration of said agent that inhibits CXCL13 activity.

23. The method of embodiment 22, wherein gastric IgA levels are increased in said subject upon administration of said agent that inhibits CXCL13 activity.

24. The method of any one of embodiments 1-23, wherein said method increases IgA antibody responses in a mucosal tissue of said subject.

25. The method of any one of embodiments 1-24, wherein said agent is a binding molecule that specifically binds to CXCR5.

26. The method of any one of embodiments 1-24, wherein said agent is a binding molecule that specifically binds to CXCL13.

27. The method of any one of embodiments 1-26, wherein said binding molecule comprises an antibody or antigen-binding fragment thereof.

28. The method of embodiment 27, wherein said antibody is chimeric, human, or humanized.

29. The method of embodiment 27 or 28, wherein said antibody specifically binds to CXCL13 and comprises a variable heavy (VH) domain having at least 90% sequence identity to the amino acid sequence set forth in SEQ ID NO: 10 or 14.

30. The method of embodiment 29, wherein said antibody that specifically binds to CXCL13 comprises a VH domain having the sequence set forth in SEQ ID NO: 14.

31. The method of any one of embodiments 27-30, wherein said antibody specifically binds to CXCL13 and comprises a variable light (VL) domain having at least 90% sequence identity to the amino acid sequence set forth in SEQ ID NO: 15, 19, or 21.

32. The method of embodiment 31, wherein said antibody that specifically binds to CXCL13 comprises a VL domain having the sequence set forth in SEQ ID NO: 19.

33. The method of embodiment 32, wherein said antibody that specifically binds to CXCL13 comprises a VH domain having the sequence set forth in SEQ ID NO: 14 and a VL domain having the sequence set forth in SEQ ID NO: 19.

34. The method of embodiment 27 or 28, wherein said antibody specifically binds to CXCL13 and comprises a VH domain having at least one of the following complementarily determining regions (CDRs):
 a) a CDR1 having at least 90% sequence identity to SEQ ID NO: 11;
 b) a CDR2 having at least 90% sequence identity to SEQ ID NO: 12; and
 c) a CDR3 having at least 90% sequence identity to SEQ ID NO: 13.

35. The method of embodiment 34, wherein said antibody that specifically binds to CXCL13 comprises a VH domain comprising a CDR1 having the sequence set forth in SEQ ID NO: 11, a CDR2 having the sequence set forth in SEQ ID NO: 12, and a CDR3 having the sequence set forth in SEQ ID NO: 13.

36. The method of any one of embodiments 27, 28, 34, and 35, wherein said antibody specifically binds to CXCL13 and comprises a VL domain having at least one of the following complementarity determining regions (CDRs):
 a) a CDR1 having at least 90% sequence identity to SEQ ID NO: 20;
 b) a CDR2 having at least 90% sequence identity to SEQ ID NO: 17; and
 c) a CDR3 having at least 90% sequence identity to SEQ ID NO: 18.

37. The method of embodiment 36, wherein said antibody that specifically binds to CXCL13 comprises a VL domain comprising a CDR1 having the sequence set forth in SEQ ID NO: 20, a CDR2 having the sequence set forth in SEQ ID NO: 17, and a CDR3 having the sequence set forth in SEQ ID NO: 18.

38. The method of embodiment 27 or 28, wherein said antibody is selected from the group consisting of MAb 5261, MAb 5378, MAb 5080, MAb 1476, and MAb 3D2.

39. The method of embodiment 38, wherein said antibody is mAb 5378.

40. The method of any one of embodiments 1-24, wherein said agent is a soluble form of CXCR5.

41. The method of any one of embodiments 1-40, wherein said agent inhibits the interaction of CXCL13 with a CXCL13 receptor.

42. The method of embodiment 41, wherein said CXCL13 receptor is CXCR5.

43. The method of any one of embodiments 1-42, wherein said agent inhibits CXCR5 receptor internalization.

44. The method of any one of embodiments 1-43, wherein said agent is administered with a pharmaceutically acceptable carrier.

45. The method of any one of embodiments 1-44, wherein said subject is an animal.

46. The method of embodiment 45, wherein said animal is a mammal.

47. The method of embodiment 46, wherein said mammal is a human.

BRIEF DESCRIPTION OF THE DRAWINGS/FIGURES

DETAILED DESCRIPTION OF THE INVENTION

Figure 1:
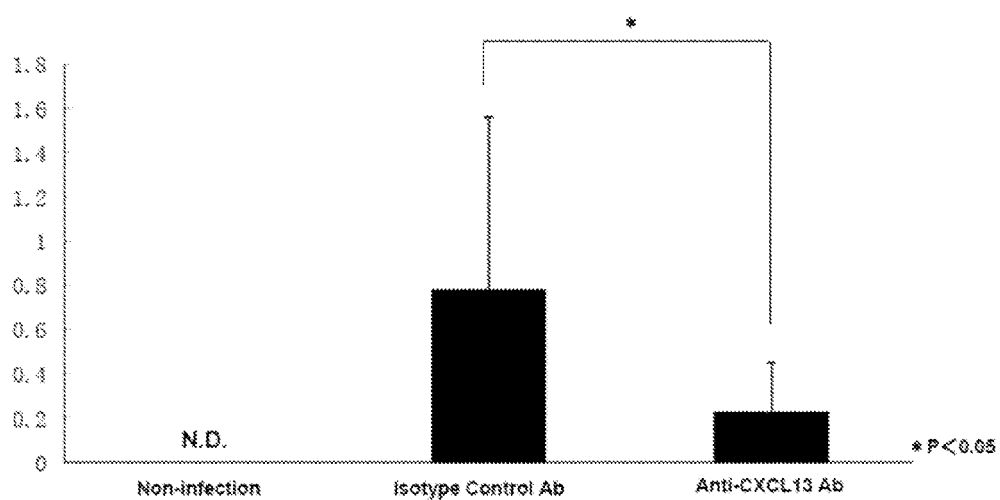
FIG. 1 shows the level of *H. suis* specific 16S ribosomal RNA in the gastric mucosa of *H. suis* infected mice treated with anti-CXCL13 antibody or isotype control antibody as determined by real-time quantitative PCR.

As demonstrated herein, agents that inhibit CXCL13 activity (e.g., an anti-CXCL13 antibody or binding fragment thereof) can reduce bacterial load and increase levels of immunoglobulin A (IgA) specific for the infective agent in mucosal tissue in an animal model for gastric infection (i.e., mice infected with *Helicobacter* bacteria (see Nobutani et al. (2010)). Administration of an anti-CXCL13 antibody also increased the expression levels of TGF-β and IL-6, which are involved in the upregulation of IgA levels, in the stomachs of uninfected mice. Therefore, agents that inhibit CXCL13 activity are also useful for generally upregulating levels of IgA in IgA deficient subjects.

The term "immunoglobulin A" or "IgA" refers to an immunoglobulin having an alpha (α) constant region in its heavy chains. The terms "immunoglobulin A" and "IgA" encompass monomeric IgA (i.e., a single molecule) and polymeric IgA (composed of more than one molecule), including, but not limited to, dimeric IgA (composed of two molecules) and trimeric IgA (composed of three molecules). IgA monomers are joined together as polymers (e.g., dimers) at the constant regions of their heavy chains by a J chain. The presence of J chains in IgA polymers allows the IgA polymer to attach to secretory component, a protein produced by epithelial cells.

The terms "immunoglobulin A" and "IgA" refer to both subclasses of IgA, IgA1 and IgA2. The light chains of IgA1 are covalently bound to its heavy chains. The light chains of IgA2, however, are bound to each other through disulfide bonds and to its heavy chains by non-covalent interactions. IgA1 predominates in serum, wherein most of it occurs as a monomer. Secretory lymphoid tissues produce more IgA2 than non-secretory lymphoid tissues.

IgA can also be classified based on its location. The terms "immunoglobulin A" and "IgA" refer to both serum IgA (i.e., found in serum) and secretory IgA, which are found in mucosal secretions (e.g., tears, saliva, colostrum, sweat, and secretions from the genitourinary tract, gastrointestinal tract, prostate and respiratory epithelium). Secretory IgA generally occurs as dimers or trimers joined by J chains and comprising secretory component. The secretory component of secretory IgA protects the immunoglobulin from being degraded by proteolytic enzymes, such as those found in the gastrointestinal tract environment. The terms "secretory immunoglobulin A" and "secretory IgA" refer to IgA that is found in mucosal secretions. Thus, the terms "secretory IgA" and "secretory immunoglobulin A" can refer to polymers of IgA, J chains that link the monomers, and the secretory component.

Naïve B cells initially express IgM and/or IgD on their surface, and once activated, the antibodies that are initially produced are primarily of the IgM isotype. If these activated B cells encounter specific signaling molecules, the B cells can undergo a "class switch" to differentiate into a cell that expresses IgG, IgA, or IgE receptors. During class switching, the constant region of the immunoglobulin heavy chain changes but the variable regions, and therefore antigenic specificity, stay the same.

Multiple studies have indicated that transforming growth factor-beta (TGF-β) induces IgA class switching and interleukin-6 (IL-6) stimulates IgA synthesis (Sonoda et al. (1989) *J Exp Med* 170:1415-1420; Beagley et al. (1989) *J Exp Med* 169:2133-2148, each of which is herein incorporated by reference in its entirety). While not being bound by any theory or mechanism of action, it is believed that agents that inhibit CXCL13 activity increase IgA levels by increasing levels of TGF-β and IL-6.

As demonstrated herein, inhibition of CXCL13 activity leads to increases in the expression levels of TGF-β and IL-6 and levels of IgA and is, therefore, useful for increasing IgA levels in a subject deficient in IgA. As used herein, "IgA deficiency" refers to reduced levels of immunoglobulin A as compared to a control subject. A subject having IgA deficiency can experience reduced levels of serum IgA, reduced levels of secretory IgA, or both, as compared to a suitable control subject. The subject may have reduced levels of secretory IgA in all secretions and at all mucosal surfaces or in only one or more type of mucosal surface and/or secretion. In some embodiments, the subject having an IgA deficiency has reduced levels of gastric IgA as compared to a suitable control.

In some embodiments, the subject having an IgA deficiency has about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or less of IgA (serum, secretory, or total) than a control subject.

One of ordinary skill in the art would understand how to select a suitable control subject in which to compare a subject believed to have an IgA deficiency. Non-limiting examples of suitable control subjects include subjects that present as healthy individuals, individuals that do not have or are believed not to have an active infection (e.g., mucosal infection) or inflammatory disorder, and a subject that does not have a genetic predisposition or a family history for IgA deficiency.

In those embodiments wherein the subject has a serum IgA deficiency, serum levels of IgA are less than about 0.1 g/L, less than about 0.09 g/L, less than about 0.08 g/L, less than about 0.07 g/L, less than about 0.06 g/L, less than about 0.05 g/L, less than about 0.04 g/L, less than about 0.03 g/L, less than about 0.02 g/L, less than about 0.01 g/L, or less.

While the term "IgA deficiency" encompasses all individuals having reduced levels of IgA as compared to a control subject, many individuals having IgA deficiency have otherwise normal levels of IgM and IgG.

IgA deficiency can be primary (inherited) or secondary (acquired). Primary IgA deficiency is genetically determined and primarily congenital, such as most forms of selective IgA deficiency. Selective IgA deficiency has been defined by the Pan-American Group for Immunodeficiency and the European Society for Immunodeficiencies as serum IgA levels of less than 0.07 g/L with normal IgM and IgG levels in individuals greater than or equal to 4 years of age (Notarangelo et al. (2009) *J Allergy Clin Immunol* 124:1161-1178, which is herein incorporated by reference in its entirety).

Certain infections or types of drugs or other agents that suppress the immune system can cause a secondary IgA deficiency, which is generally transient. Exposure to immunosuppressants, D-penicillamine, sulfasalazine, aurothioglucose, fenclofenac, gold, captopril, zonisamide, phenytoin, valproic acid, thyroxine, chloroquine, carabamazepine, hydantoin, levamisole, ibuprofen, salicylic acid, benzene, and cyclosporin A, for example, can result in a transient IgA deficiency, which resolves upon clearance of the drug. Non-limiting examples of infections that can cause secondary IgA deficiency include rubella, cytomegaloviruses, *Toxoplasma gondii*, and Epstein-Barr virus.

In some embodiments, the subject has IgA deficiency secondary to a mucosal infection. In some of these embodiments, the mucosal infection is a bacterial infection. In certain embodiments, the bacterial infection that results in a secondary IgA deficiency is a *Heliobacter* infection, such as *H. pylori*, *H. heilmannii*, or *H. suis*.

In some embodiments of the presently disclosed methods, administration of an agent that inhibits CXCL13 activity to a subject having a deficiency in IgA results in an increase in total IgA (serum and secretory). In other embodiments, the administration of the CXCL13 inhibitory agent results in an increase in secretory IgA. In particular embodiments, the subject that has been administered a CXCL13 inhibitory agent experiences an increase in gastric levels of IgA. In those embodiments wherein the subject is undergoing attack by an infectious agent, the administration of a CXCL13 inhibitory agent can increase levels of IgA specific for the infectious agent, which in some embodiments can lead to increased clearance of the infectious agent.

In certain embodiments, administration of an agent that inhibits CXCL13 activity increases serum, secretory, or total IgA levels by about 1%, about 2%, about 3%, about 4%, about 5%, about 10%, about 15%, about 20%, about 30%, about 40%, about 50%, about 60%, about 70%, about 80%, about 90%, about 100%, or more in the subject.

Given that inhibitors of CXCL13 activity can increase IgA levels, agents that inhibit CXCL13 activity can be used to treat inflammatory disorders in subjects having a deficiency in IgA. Inflammatory diseases are characterized by inflammation and tissue destruction, or a combination thereof. By "anti-inflammatory activity" is intended a reduction or prevention of inflammation. "Inflammatory disease" or "inflammatory disorder" includes any inflammatory immune-mediated process where the initiating event or target of the immune response involves non-self antigen(s), including, for example, alloantigens, xenoantigens, viral antigens, bacterial antigens, self antigens, unknown antigens, or allergens. In some embodiments, the inflammatory disorder is an infectious disease. In one embodiment, the inflammatory disorder is associated with and/or caused by a mucosal infection (e.g., bacterial, viral). In some embodiments, the inflammatory disease is associated with and/or caused by a bacterial infection, e.g., an *E. coli* or a *Helicobacter* infection, e.g., a *H. pylori, H. heilmannii, H. acinonychis, H. anseris, H. aurati, H. baculiformis, H. bilis, H. bizzozeronii, H. brantae, H. candadensis, H. canis, H. cholecystus, H. cinaedi, H. cynogastricus, H. equorum, H. felis, H. fenelliae, H. ganmani, H. hepaticus, H. mesocricetorum, H. marmotae, H. muridarum, H. mustelae, H. pametensis, H. pullorum, H. rappini, H. rodentium, H. salomonis, H. suis, H. trogontum, H. typhlonius*, and *H. winghamensis* infection. In certain embodiments, the *Helicobacter* infection is a *H. pylori*, a *H. heilmannii*, or a *H. suis* infection.

In a further embodiment, the *Helicobacter*-associated inflammatory disease is MALT lymphoma (e.g., gastric MALT lymphoma), a gastric cancer (e.g., esophageal or stomach cancer), a gastric or duodenal ulcer, gastritis (an inflammation of the stomach lining), or a gastric lesion (see, e.g., Chen et al., *J Clin Pathol* 55(2):133-7 (2002); Genta et al., *Hum Pathol* 24(6):577-83 (1993); Okiyama et al., *Pathol Int* 55(7):398-404 (2005)).

In some embodiments, administration of an agent that inhibits CXCL13 activity results in a reduction in the burden of an infectious agent (e.g., bacteria) in the subject. In some of these embodiments, administration of the anti-CXCL13 agent results in a reduction in the burden of an infectious agent (e.g., bacteria) in the mucosa and in some of these embodiments, levels of the infectious agent (e.g., bacteria) in at least one mucosal secretion is reduced. In some of these embodiments, administration of an anti-CXCL13 agent to a subject having an infection results in a reduction in the levels of an infectious agent (e.g., bacteria) by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or more in the subject.

In some of those embodiments wherein a CXCL13 inhibitory agent is administered to a subject having an IgA deficiency, the CXCL13 inhibitory agent increases IgA antibody responses in a mucosal tissue of said subject. In these embodiments, the levels of antigen-specific IgA levels (e.g., IgA that specifically recognize an infectious agent) increase, which in some embodiments, results in more efficient clearance of an infectious agent. The term "inflammatory disorder" or "inflammatory disease" includes, but is not limited to, allergic reactions to allergens. Allergic reactions are mediated by immunoglobulin E (IgE). IgA can bind allergenic substances, thereby preventing allergens from binding IgE or activating T cells responsible for delayed-type hypersensitivity. Therefore, the administration of an agent that inhibits CXCL13 activity resulting in an increase in IgA levels can be used to treat or prevent allergic reactions, including, but not limited to, asthma, allergic rhinitis, allergic sinusitis, contact dermatitis, eczema, urticaria, dyspnea, vomiting, bloating, and diarrhea, in response to various allergens, including, but not limited to, certain foods, drugs, insect stings, pollens, latex, and plant toxins.

Further, for purposes of the present invention, the term "inflammatory disease(s)" includes, but is not limited to, "autoimmune disease(s)" also referred to herein as "autoimmune disorder(s)" As used herein, the term "autoimmunity" is generally understood to encompass inflammatory immune-mediated processes involving "self" antigens. In autoimmune diseases, self antigen(s) trigger host immune responses.

In some embodiments, the inflammatory disease is the result of a genetically determined selective IgA-deficiency which may prevent clearing of an infectious agent or precipitate an autoimmune disease, including, but not limited to, rheumatoid arthritis, systemic lupus erythematosus, Graves disease, Type 1 diabetes, myasthenia gravis, Sjogren syndrome, multiple sclerosis, or celiac sprue (Wang et al. (2011) *Mol Med* 17(11-12):1383-1396, which is herein incorporated by reference in its entirety). In some embodiments, the inflammatory disease is a B cell-mediated inflammatory disease. As used herein, the term "B cell-mediated inflammatory disease" is an inflammatory disease as described herein, wherein the pathogenesis, progression, or both the pathogenesis and progression of the disease is primarily dependent upon the activity of B cells. Non-limiting examples of B cell-mediated inflammatory diseases include those that are characterized by the production of autoantibodies.

A "B cell" is a lymphocyte that matures within the bone marrow, and includes a naive B cell, memory B cell, or effector B cell (plasma cells). The B cell herein may be a normal or non-malignant B cell.

A "B-cell surface marker" or "B-cell surface antigen" herein is an antigen expressed on the surface of a B cell that can be targeted with an antagonist that binds thereto. Exemplary B-cell surface markers include, for instance, CD10, CD19, CD20, CD21, CD22, CD23, CD24, CD37, CD40, CD53, CD72, CD73, CD74, CDw75, CDw76, CD77, CDw78, CD79a, CD79b, CD80, CD81, CD82, CD83, CDw84, CD85 and CD86, and CXCR5. The B-cell surface marker of particular interest is preferentially expressed on B cells compared to other non-B-cell tissues of a mammal and may be expressed on both precursor B cells and mature B cells. The preferred B-cell surface markers herein are CD19 and CXCR5. For purposes of the present invention, the term "inflammatory disease(s)" includes, but is not limited to, "autoimmune disease(s)."

According to the presently disclosed methods, an agent that inhibits CXCL13 activity is administered to a subject having an IgA deficiency. In certain embodiments, an agent is administered to a subject in need thereof for the treatment of an inflammatory disorder.

In some embodiments, treatment includes the application or administration of an agent that inhibits CXCL13 activity (e.g., an anti-CXCL13 or anti-CXCR5 binding molecule) to a subject, or application or administration of the agent to an isolated tissue or cell line from a subject, where the subject has an inflammatory disorder, a symptom of an inflammatory disorder, or a predisposition toward an inflammatory disorder. In another embodiment, treatment is also intended to include the application or administration of a pharmaceutical composition comprising the agent that inhibits CXCL13 activity (e.g., an anti-CXCL13 or anti-CXCR5 binding molecule) to a subject, or application or administration of a pharmaceutical composition comprising the agent to an isolated tissue or cell line from a subject, who has an inflammatory disorder, a symptom of an inflammatory disorder, or a predisposition toward an inflammatory disorder.

In accordance with the methods of the present invention, at least one agent that inhibits CXCL13 activity (e.g., anti-CXCL13 or anti-CXCR5 binding molecule) is used to promote a positive therapeutic response with respect to treatment or prevention of an IgA deficiency and/or an inflammatory disorder. By "positive therapeutic response" with respect to an inflammatory disease is intended an improvement in the disease in association with the anti-inflammatory activity, anti-angiogenic activity, anti-apoptotic activity, or the like, of the administered agent, and/or an improvement in the symptoms associated with the disease. That is, an anti-proliferative effect, the prevention of further proliferation of the CXCL13-expressing cell, a reduction in the inflammatory response including but not limited to reduced secretion of inflammatory cytokines, adhesion molecules, proteases, immunoglobulins (in instances where the CXCL13 bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in the number of ectopic lymphoid follicles, reduction in the number of B cells present in affected tissues, reduction in the migration of B cells to the affected tissues, reduction in and/or a decrease in one or more symptoms mediated by stimulation of CXCL13-expressing cells can be observed. By "positive therapeutic response" with respect to an infectious disease is intended clearance of the infectious agent, for example, a bacteria and an improvement in the disease symptoms associated with the infection.

Such positive therapeutic responses are not limited to the route of administration and may comprise administration to the donor, the donor tissue (such as for example organ perfusion), the host, any combination thereof, and the like. Clinical response can be assessed using screening techniques such as magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the agent that inhibits CXCL13 activity (e.g., anti-CXCL13 or anti-CXCR5 binding molecule) may experience the beneficial effect of an improvement in the symptoms associated with the inflammatory disorder.

As used herein, the terms "treat" or "treatment" refer to both therapeutic treatment and prophylactic or preventative measures, wherein the object is to prevent or slow down (lessen), reduce the exacerbation of, or prevent the recurrence of an undesired physiological change or disorder, such as the progression of an inflammatory disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cows, and so on.

As used herein, phrases such as "a subject that would benefit from administration of an agent that inhibits CXCL13 activity" and "an animal in need of treatment" includes subjects, such as mammalian subjects, that would benefit from administration of an agent that inhibits CXCL13 activity (e.g., an anti-CXCL13 or anti-CXCR5 antibody) for treatment, i.e., palliation or prevention of an inflammatory disorder. As described in more detail herein, an anti-CXCL13 or anti-CXCR5 antibody can be used in unconjugated form or can be conjugated, e.g., to a drug, prodrug, or an isotope.

The presently disclosed methods utilize an agent that inhibits CXCL13 activity. CXCL13 (otherwise known as homeostatic B Cell-attracting chemokine 1 (BCA-1) or ANGIE, BLC, BLR1L, ANGIE2, or Scyb13) is constitutively expressed in secondary lymphoid organs (e.g., spleen, lymph nodes, and Peyer's patches) by follicular dendritic cells (FDCs) and macrophages. See Gunn et al., *Nature* 391:799-803 (1998) and Carlsen et al., *Blood* 104(10):3021-3027 (2004). CXCL13 primarily acts through the G-protein-coupled CXCR5 receptor (Burkitt's lymphoma receptor 1). CXCR5 is expressed, e.g., on mature B lymphocytes, CD4+ follicular helper T cells (Thf cells), a minor subset of CD8+ T cells, and activated tonsillar Treg cells. See Legler et al., *J. Exp. Med.* 187:655-660 (1998); Förster et al., *Blood* 84:830-840 (1994); Fazilleau et al., *Immunity* 30:324-335 (2009); Ansel et al., *J. Exp. Med.* 190:1123-1134 (1999); Lim et al., *J. Clin. Invest.* 114(11):1640-1649 (2004); and R. Förster, Chapter in Academic Press Cytokine Reference, August 2000.

As used herein, the terms "CXCL13" and "CXCL13 polypeptide" are used interchangeably. In certain embodiments, CXCL13 may include a full-sized CXCL13 or a fragment thereof, or a CXCL13 variant polypeptide, wherein the fragment of CXCL13 or CXCL13 variant polypeptide retains some or all functional properties of the full-sized CXCL13. The human CXCL13 polynucleotide and polypeptide sequences (SEQ ID NOs: 1 and 2, respectively) have been described, see, e.g., Legler, et. al., *J. Exp. Med.* 187(4):655-660 (1998). The mouse CXCL13 polynucleotide and polypeptide sequences (SEQ ID NOs: 3 and 4, respectively) have been described, see, e.g., Gunn, et. al., *Nature* 391(6669):799-803 (1998). Furthermore, the cynomolgus monkey CXCL13 polypeptide sequence has been described as shown in SEQ ID NO: 5.

As used herein, the terms "CXCR5" and "CXCR5 polypeptide" are used interchangeably. In certain embodiments, CXCR5 may include a full-sized CXCR5 or a fragment thereof, or a CXCR5 variant polypeptide, wherein the fragment of CXCR5 or CXCR5 variant polypeptide retains some or all functional properties of the full-sized CXCR5. The terms "CXCR5" and "CXCR5 polypeptide" also encompass a soluble form of CXCR5. As used herein, the term "soluble form of CXCR5" is a form of CXCR5 that is not bound to a plasma membrane. Full-length CXCR5 is a seven transmembrane receptor. Therefore, non-limiting examples of a soluble form of CXCR5 include fragments of CXCR5 that consist essentially of the extracellular domain (e.g., about the first 60 amino acids). The human CXCR5 polynucleotide and polypeptide sequences are known in the art and provided herein as SEQ ID NOs: 6 and 7, respectively. The murine CXCR5 polynucleotide and polypeptide sequences are known in the art and provided herein as SEQ ID NOs: 8 and 9, respectively.

Agents useful for the inhibition of CXCL13 activity include small molecules, polypeptides, and polynucleotides. In certain embodiments, the agent blocks the binding of CXCL13 to its receptor. In some embodiments, the agent blocks the interaction between CXCL13 and CXCR5. In particular embodiments, the agent is a specific binding molecule that specifically binds CXCL13 or CXCR5. In some of these embodiments, the agent is an anti-CXCL13 or anti-CXCR5 antibody or an antigen-binding fragment thereof. In other embodiments, the agent is a soluble form of CXCR5.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide useful in the presently disclosed methods may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides useful in the presently disclosed methods are fragments, derivatives, analogs, or variants of polypeptides, and any combination thereof. The terms "fragment," "variant," "derivative," and "analog" when referring to anti-CXCL13 or anti-CXCR5 antibodies or antibody polypeptides include any polypeptides that retain at least some of the antigen-binding properties of the corresponding antibody or antibody polypeptide. Fragments of polypeptides include proteolytic fragments, as well as deletion fragments, in addition to specific antibody fragments discussed elsewhere herein. Variants of anti-CXCL13 or anti-CXCR5 antibodies include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs." As used herein a "derivative" of an anti-CXCL13 or anti-CXCR5 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-CXCL13 and anti-CXCR5 antibodies and antibody polypeptides, may include polypeptides that have been altered so as to exhibit additional features not found on the reference antibody or antibody polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-CXCL13 or anti-CXCR5 binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions useful in the presently disclosed methods can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid useful in the presently disclosed methods may encode heterologous coding regions, either fused or unfused to a nucleic acid encoding an anti-CXCL13 or anti-CXCR5 antibody or fragment, variant, or derivative thereof. Heterologous coding regions include without limitation specialized elements or motifs, such as a secretory signal peptide or a heterologous functional domain.

In certain embodiments, the polynucleotide or nucleic acid useful in the presently disclosed methods is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide useful in the presently disclosed methods is RNA, for example, in the form of messenger RNA (mRNA).

Polynucleotide and nucleic acid coding regions useful in the presently disclosed methods may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

A "binding molecule" or "antigen binding molecule" refers in its broadest sense to a molecule that specifically binds an antigenic determinant. In one embodiment, the binding molecule specifically binds to CXCL13 (also called BCA-1). In another embodiment, the binding molecule specifically binds to CXCR5. In another embodiment, a binding molecule useful in the presently disclosed methods is an antibody or an antigen binding fragment thereof, e.g., an anti-CXCL13 or anti-CXCR5 antibody. In another embodiment, a binding molecule comprises at least one heavy or light chain CDR of an antibody molecule. In another embodiment, a binding molecule comprises at least two CDRs from one or more antibody molecules. In another embodiment, a binding molecule comprises at least three CDRs from one or more antibody molecules. In another embodiment, a binding molecule comprises at least four CDRs from one or more antibody molecules. In another embodiment, a binding molecule comprises at least five CDRs from one or more antibody molecules. In another embodiment, a binding molecule comprises at least six CDRs from one or more antibody molecules. In certain embodiments, one or more of the CDRs is from MAb 5261, MAb 5378, MAb 5080, MAb 1476, or 3D2.

In some embodiments, the presently disclosed methods involve certain anti-CXCL13 or anti-CXCR5 antibodies, or antigen-binding fragments, variants, or derivatives thereof. Unless specifically referring to full-sized antibodies such as naturally occurring antibodies, the terms "anti-CXCL13 antibodies" and "anti-CXCR5 antibodies" encompass full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of known anti-CXCL13 or anti-CXCR5 antibody molecules (e.g., the VH regions and/or VL regions), which antibodies or fragments thereof immunospecifically bind to a CXCL13 or CXCR5 polypeptide or fragment or variant thereof. Standard techniques known to those of skill in the art can be used to introduce mutations in the nucleotide sequence encoding a human anti-CXCL13 or anti-CXCR5 antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitutions, discussed further below. Alternatively, mutations can be introduced randomly along all or part of the coding sequence, such as by saturation mutagenesis, and the resultant mutants can be screened for biological activity to identify mutants that retain activity (e.g., the ability to bind a CXCL13 or CXCR5 polypeptide, e.g., human, murine, or both human and murine CXCL13 or CXCR5). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma$1-$\gamma$4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernible to the skilled artisan in view of the instant disclosure and, accordingly, are within the scope of the instant invention. The use of all immunoglobulin classes are clearly within the scope of the presently disclosed methods, however, the following discussion will generally be directed to the IgG class of immunoglobulin molecules. With regard to IgG, a standard immunoglobulin molecule comprises two identical light chain polypeptides of a molecular weight of approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B-cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated herein, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|         | Kabat  | Chothia |
|---------|--------|---------|
| VH CDR1 | 31-35  | 26-32   |
| VH CDR2 | 50-65  | 52-58   |
| VH CDR3 | 95-102 | 95-102  |
| VL CDR1 | 24-34  | 26-32   |
| VL CDR2 | 50-56  | 50-52   |
| VL CDR3 | 89-97  | 91-96   |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-CXCL13 antibody or antigen-binding fragment, variant, or derivative thereof of the present invention are according to the Kabat numbering system.

Antibodies or antigen-binding fragments, variants, or derivatives thereof useful in the presently disclosed methods include, but are not limited to, polyclonal, monoclonal, multispecific, human, humanized, primatized, or chimeric antibodies, single-chain antibodies, epitope-binding fragments, e.g., Fab, Fab' and F(ab')2, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-CXCL13 or anti-CXCR5 antibodies). ScFv molecules are known in the art and are described, e.g., in U.S. Pat. No. 5,892,019 Immunoglobulin or antibody molecules used in the presently disclosed methods can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the presently disclosed methods may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide useful in the presently disclosed methods comprises a polypeptide chain comprising a CH3 domain. Further, a binding polypeptide for use in the presently disclosed methods may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-CXCL13 or anti-CXCR5 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers useful in the presently disclosed methods are not identical. For example, each monomer may comprise a different target binding site, forming, for example, a bispecific antibody.

The heavy chain portions of a binding molecule for use in the methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-CXCL13 or anti-CXCR5 antibodies, or antigen-binding fragments, variants, or derivatives thereof useful in the presently disclosed methods may be described or specified in terms of the epitope(s) or portion(s) of an antigen, e.g., a target polypeptide disclosed herein (e.g., CXCL13 or CXCR5) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-CXCL13 or anti-CXCR5 antibodies useful in the presently disclosed methods may contain a sequence of at least 4, at least 5, at least 6, at least 7, more preferably at least 8, at least 9, at least 10, at least 15, at least 20, at least 25, or between about 15 to about 30 contiguous or non-contiguous amino acids of CXCL13 or CXCR5.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with a $K_D$ that is at least one order of magnitude less than the antibody's $K_D$ for the second epitope. In another non-limiting example, an antibody may be considered to bind a first epitope preferentially if it binds the first epitope with a $K_D$ that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an k(off) that is at least one order of magnitude less than the antibody's k(off) for the second epitope. In another non-limiting example, an antibody may be considered to bind a first epitope preferentially if it binds the first epitope with an k(off) that is at least two orders of magnitude less than the antibody's k(off) for the second epitope. An antibody or antigen-binding fragment, variant, or derivative useful in the methods disclosed herein may be said to bind a target polypeptide disclosed herein (e.g., CXCL13 or CXCR5, e.g., human, murine, or both human and murine CXCL13 or CXCR5) or a fragment or variant thereof with an off rate (k(off)) of less than or equal to $5 \times 10^{-2}$ sec$^{-1}$, $10^{-2}$ sec$^{-1}$, or $5 \times 10^{-3}$ sec$^{-1}$. In certain embodiments, the k(off) is less than or equal to about $3 \times 10^{-2}$, e.g., wherein the antibody is 3D2 and the CXCL13 is human or mouse. In another embodiment, the k(off) is less than or equal to about $3 \times 10^{-3}$, e.g., wherein the antibody is MAb 5261 and the CXCL13 is human or mouse. In another embodiment, the k(off) is less than or equal to about $4 \times 10^{-3}$, e.g., wherein the antibody is MAb 5378 and the CXCL13 is human or mouse. In one embodiment, an antibody useful in the presently disclosed methods may be said to bind a target polypeptide disclosed herein (e.g., CXCL13, e.g., human, murine, or both human and murine CXCL13) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or or antigen-binding fragment, variant, or derivative useful in the methods disclosed herein may be said to bind a target polypeptide disclosed herein (e.g., CXCL13 or CXCR5, e.g., human, murine, or both human and murine CXCL13 or CXCR5) or a fragment or variant thereof with an on rate (k(on)) of greater than or equal to $10^3$M$^{-1}$ sec$^{-1}$, $5 \times 10^3$ M$^{-1}$ sec$^{-1}$, $10^4$M$^{-1}$ sec$^{-1}$, $5 \times 10^4$M$^{-1}$ sec$^{-1}$, $10^5$M$^{-1}$ sec$^{-1}$, $5 \times 10^5$ M$^{-1}$ sec$^{-1}$, $10^6$M$^{-1}$ sec$^{-1}$ or $5 \times 10^6$M$^{-1}$ sec$^{-1}$. In certain embodiments, the k(on) is greater than or equal to about 5×10⁵, e.g., wherein the antibody is 3D2 and the CXCL13 is human; or the k(on) is greater than or equal to about 1×10⁵, e.g., wherein the antibody is 3D2 and the CXCL13 is mouse. In another embodiment, the k(on) is greater than or equal to about 1×10⁶, e.g., wherein the antibody is MAb 5261 and the CXCL13 is human or mouse. In another embodiment, the k(on) is greater than or equal to about 1×10⁶, e.g., wherein the antibody is MAb 5378 and the CXCL13 is human or mouse. In one embodiment, an antibody useful in the presently disclosed methods may be said to bind a target polypeptide disclosed herein (e.g., CXCL13, e.g., human, murine, or both human and murine CXCL13) or a fragment or variant thereof with an on rate (k(on)) greater than or equal to $10^5$ $M^{-1}$ $sec^{-1}$, $5\times10^5$ $M^{-1}$ $sec^{-1}$, $10^6 M^{-1}$ $sec^{-1}$, or $5\times10^6$ $M^{-1}$ $sec^{-1}$ or $10^7$ $M^{-1}$ $sec^{-1}$.

An antibody is said to competitively inhibit binding of a reference antibody, e.g., an anti-CXCL13 or anti-CXCR5 antibody, to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-CXCL13 or anti-CXCR5 antibodies or antigen-binding fragments, variants, or derivatives thereof useful in the presently disclosed methods may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-CXCL13 or anti-CXCR5 binding molecules, e.g., antibodies or antigen-binding fragments, variants or derivatives thereof, useful in the presently disclosed methods may also be described or specified in terms of their binding affinity to a polypeptide, e.g., CXCL13 or CXCR5, e.g., human, murine, or both human and murine CXCL13 or CXCR5. In certain embodiments, the binding affinities of the antibodies or antigen-binding fragments thereof useful in the presently disclosed methods include those with a dissociation constant or Kd less than or no greater than $5\times10^{-2}$ M, $10^{-2}$ M, $5\times10^{-3}$ M, $10^{-3}$ M, $5\times10^{-4}$ M, $10^4$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In one embodiment, the anti-CXCL13 or anti-CXCR5 binding molecule, e.g., an antibody or antigen binding fragment thereof, useful in the presently disclosed methods binds human CXCL13 or CXCR5 with a Kd of less than about $5\times10^{-9}$ M to about $5\times10^{-10}$M, e.g., wherein the antibody is MAb 5261 and the Kd is less than or equal to about $5\times10^{-9}$M. In another embodiment, the anti-CXCL13 or anti-CXCR5 binding molecule, e.g., an antibody or antigen binding fragment thereof, binds murine CXCL13 or CXCR5 with a Kd of less than about $5\times10^{-7}$ M to about $9\times10^{-9}$M, e.g., wherein the antibody is MAb 5261 and the Kd is less than or equal to about $8\times10^{-9}$M.

Anti-CXCL13 or anti-CXCR5 antibodies or antigen-binding fragments, variants or derivatives thereof useful in the presently disclosed methods may be "multispecific," e.g., bispecific, trispecific, or of greater multispecificity, meaning that it recognizes and binds to two or more different epitopes present on one or more different antigens (e.g., proteins) at the same time. Thus, whether an anti-CXCL13 or anti-CXCR5 antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains present in a binding polypeptide or CXCL13 or CXCR5 binding molecule, e.g., an antibody or antigen binding fragment thereof. Each binding domain specifically binds one epitope. When a binding polypeptide or CXCL13 or CXCR5 binding molecule comprises more than one binding domain, each binding domain may specifically bind the same epitope, for an antibody with two binding domains, termed "bivalent monospecific," or to different epitopes, for an antibody with two binding domains, termed "bivalent bispecific." An antibody or antigen binding fragment thereof may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731, 168; 5,807,706; 5,821,333; and U.S. Patent Appl. Publ. Nos. 2003/020734 and 2002/0155537, the disclosures of all of which are incorporated by reference herein. Bispecific tetravalent antibodies and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., *J. Immunol.* 147:60-69 (1991); U.S. Pat. Nos. 4,474,893; 4,714,681; 4,925,648; 5,573,920; 5,601,819; Kostelny et al., *J. Immunol.* 148: 1547-1553 (1992).

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In certain embodiments the target binding region or site will be from a non-human source (e.g., mouse or primate) and the constant region is human (for example, monoclonal antibody (MAb) 1476).

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site. In certain embodiments, the humanized antibody comprises 1, 2, or 3 CDRs from a donor variable heavy domain. In another embodiment, the humanized antibody comprises 1, 2, or 3 CDRs from a donor variable light domain.

It is further recognized that the framework regions within the variable domain in a heavy or light chain, or both, of a humanized antibody may comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the CXCL13 or CXCR5 antigen. A human framework region that has been engineered in this manner would thus comprise a mixture of human and donor framework residues, and is referred to herein as a "partially human framework region."

For example, humanization of an anti-CXCL13 or anti-CXCR5 antibody can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988), each of which is herein incorporated by reference in its entirety), by substituting rodent or mutant rodent CDRs or CDR sequences for the corresponding sequences of a human anti-CXCL13 antibody. See also U.S. Pat. Nos. 5,225,539; 5,585,089; 5,693,761; 5,693,762; and 5,859,205; herein incorporated by reference. The resulting humanized anti-CXCL13 or anti-CXCR5 antibody would comprise at least one rodent or mutant rodent CDR within the fully human framework regions of the variable domain of the heavy and/or light chain of the humanized antibody. In some instances, residues within the framework regions of one or more variable domains of the humanized anti-CXCL13 or anti-CXCR5 antibody are replaced by corresponding non-human (for example, rodent) residues (see, for example, U.S. Pat. Nos. 5,585,089; 5,693,761; 5,693,762; and 6,180,370, each of which is herein incorporated by reference in its entirety), in which case the resulting humanized anti-CXCL13 antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some or all CDR residues and possibly some framework residues are substituted by residues from analogous sites in rodent antibodies. See, for example, U.S. Pat. Nos. 5,225,539; 5,585,089; 5,693,761; 5,693,762; and 5,859,205. See also U.S. Pat. No. 6,180,370, and International Publication No. WO 01/27160, where humanized antibodies and techniques for producing humanized antibodies having improved affinity for a predetermined antigen are disclosed.

Commercial antibodies that bind CXCL13 have been disclosed in the art, e.g., rat anti-mouse MAb 470 (R & D Systems) and mouse anti-human MAb 801 (R & D Systems). In addition, murine anti-CXCL13 antibodies are disclosed in U.S. Patent Application Publication No. 2008 0227704 A1, which is herein incorporated by reference in its entirety. The monoclonal anti-CXCL13 antibodies MAb 5261, MAb 5378, MAb 5080, MAb 1476, and 3D2 are disclosed in International Application Publication No. WO 2012/031099, which is herein incorporated by reference in its entirety.

Monoclonal antibody 5261 comprises a variable heavy (VH) domain having the sequence set forth in SEQ ID NO: 14 and a variable light (VL) domain having the sequence set forth in SEQ ID NO: 19. MAb 5261 comprises a human IgGamma1-F allotype constant region within its heavy chain and a human kappa constant region within its light chain. Monoclonal antibody 5378 comprises a variable heavy (VH) domain having the sequence set forth in SEQ ID NO: 14 and a variable light (VL) domain having the sequence set forth in SEQ ID NO: 19. MAb 5378 comprises a murine IgG2a constant region within its heavy chain and a murine kappa constant region within its light chain. MAb 5080 comprises a VH domain having the sequence set forth in SEQ ID NO: 14 and a VL domain having the sequence set forth in SEQ ID NO: 21. MAb 5080 comprises a human IgG1 constant region within its heavy chain and a human kappa constant region within its light chain. Monoclonal antibody 1476 comprises a VH domain having the sequence set forth in SEQ ID NO: 10 and a VL domain having the sequence set forth in SEQ ID NO: 15. MAb 1476 comprises a human IgG1 constant region within its heavy chain and a human kappa constant region within its light chain. Monoclonal antibody 3D2 comprises a VH domain having the sequence set forth in SEQ ID NO: 10 and a VL domain having the sequence set forth in SEQ ID NO: 15. MAb 3D2 comprises a murine IgG1 constant region within its heavy chain and a murine kappa constant region within its light chain.

In some embodiments, the presently disclosed methods utilize the MAb 5261, MAb 5378, MAb 5080, MAb 1476, or 3D2 anti-CXCL13 monoclonal antibodies.

In some embodiments, the antibodies used in the presently disclosed methods comprise anti-CXCL13 antibodies or antigen-binding fragments, variants, or derivatives thereof that bind to CXCL13. In certain embodiments the anti-CXCL13 antibodies bind human, primate, murine, or both human and murine CXCL13. In certain embodiments, the anti-CXCL13 antibodies useful in the presently disclosed methods are humanized. In other embodiments, the anti-CXCL13 antibodies block CXCL13 binding to its receptor, e.g., CXCR5. In certain embodiments, the anti-CXCL13 antibodies useful in the presently disclosed methods are MAb 5261, MAb 5378, MAb 5080, MAb 1476, or 3D2, or antigen-binding fragments, variants, or derivatives thereof. In one embodiment, the presently disclosed methods utilize an isolated binding molecule, e.g., an antibody or antigen binding fragments, variants, and derivatives thereof, which specifically binds to the same CXCL13 or CXCR5 epitope as a reference antibody, e.g., MAb 5261, MAb 5378, MAb 5080, MAb 1476, or 3D2. In another embodiment, the presently disclosed methods involve an isolated binding molecule, e.g., an antibody or antigen binding fragment thereof, which specifically binds to CXCL13, and competitively inhibits a reference antibody, e.g., MAb 5261, MAb 5378, MAb 5080, MAb 1476, or 3D2, from specifically binding to CXCL13, e.g., human, primate, murine, or both human and murine CXCL13.

In certain embodiments, the binding molecule useful in the presently disclosed methods has an amino acid sequence that has at least about 80%, about 85%, about 88%, about 89%, about 90%, about 91%, about 92%, about 93%, about 94%, or about 95% sequence identity of an amino acid sequence for the reference anti-CXCL13 antibody molecule. In a further embodiment, the binding molecule shares at least about 96%, about 97%, about 98%, about 99%, or 100% sequence identity to a reference antibody. In certain embodiments, the reference antibody is MAb 5261, MAb 5378, MAb 5080, MAb 1476, or 3D2.

In another embodiment, the presently disclosed methods utilize an antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 10 or 14.

In another embodiment, the presently disclosed methods utilize an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 11, 12, or 13.

In another embodiment, the presently disclosed methods utilize an antibody or antigen-binding fragment thereof comprising, consisting essentially of, or consisting of an immunoglobulin heavy chain variable domain (VH domain), where the VH domain has an amino acid sequence that is at least about 80%, about 85%, about 90%, about 95%, about 96%, about 97%, about 98%, about 99%, or identical to SEQ ID NO: 10 or 14.

In another embodiment, the presently disclosed methods utilize an antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to CDR1, CDR2 or CDR3 of SEQ ID NO: 10 or 14

In another embodiment, the presently disclosed methods utilize an antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 11, 12, or 13.

In another embodiment, the presently disclosed methods utilize an antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 15, 19, or 21.

In another embodiment, the presently disclosed methods utilize an antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 16, 17, 18, or 20.

In another embodiment, the presently disclosed methods utilize an antibody or antigen-binding fragment thereof comprising, consisting essentially of, or consisting of an immunoglobulin light chain variable domain (VL domain), where the VL domain has an amino acid sequence that is at least about 80%, about 85%, about 90%, about 95%, about 96%, about 97%, about 98%, about 99%, or identical to SEQ ID NO: 15, 19, or 21.

In another embodiment, the presently disclosed methods utilize an antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to CDR1, CDR2 or CDR3 of SEQ ID NO: 15, 19, or 21.

In another embodiment, the presently disclosed methods utilize an antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 16, 17, 18, or 20.

In a further embodiment, the presently disclosed methods utilize an antibody or antigen-binding fragment thereof comprising, consisting essentially of, or consisting of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 15, 19, or 21, wherein an anti-CXCL13 antibody comprising the encoded VL domain specifically or preferentially binds to CXCL13.

In certain embodiments, the presently disclosed methods utilize an antibody or antigen-binding fragment thereof comprising, consisting essentially of, or consisting of a VH domain that has the amino acid sequence set forth in SEQ ID NO: 14 and a VL domain that has the amino acid sequence set forth in SEQ ID NO: 19. In some of these embodiments, the antibody comprises a human IgG1 constant region within its heavy chain and a human kappa constant region within its light chain.

In particular embodiments, the presently disclosed methods utilize an antibody or antigen-binding fragment thereof comprising, consisting essentially of, or consisting of a VH domain comprising a CDR1 having the amino acid sequence set forth in SEQ ID NO: 11, a CDR2 having the amino acid sequence set forth in SEQ ID NO: 12, and a CDR3 having the amino acid sequence set forth in SEQ ID NO: 13; and a VL domain comprising a CDR1 having the amino acid sequence set forth in SEQ ID NO: 20, a CDR2 having the amino acid sequence set forth in SEQ ID NO: 17, and a CDR3 having the amino acid sequence set forth in SEQ ID NO: 18. In some of these embodiments, the antibody comprises a human IgG1 constant region within its heavy chain and a human kappa constant region within its light chain.

Suitable biologically active variants of reference anti-CXCL13 or anti-CXCR5 antibodies can be used in the presently disclosed methods. Such variants will retain the desired binding properties of the parent anti-CXCL13 or anti-CXCR5 antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of an anti-CXCL13 or anti-CXCR5 binding molecule, e.g., an antibody or antigen-binding fragment thereof, or polypeptides of interest, modifications are made such that variants continue to possess the desired properties, e.g., being capable of specifically binding to a CXCL13 or CXCR5, e.g., human, primate, murine, or both human and murine CXCL13 or CXCR5. Obviously, any mutations made in the DNA encoding the variant polypeptide must not place the sequence out of reading frame and preferably will not create complementary regions that could produce secondary mRNA structure. See, e.g., EP Pat. No. EP0075444 B1.

Methods for measuring anti-CXCL13 or anti-CXCR5 binding molecule, e.g., an antibody or antigen-binding fragment thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

Through its receptor, CXCR5, which is found on a variety of immune cells (e.g., B cells, follicular helper T cells, and recently-activated T cells), CXCL13 induces intracellular changes necessary for maintenance of immune system homeostasis, lymphoid organogenesis, leukocyte trafficking and chemotactic migration as well as development of secondary lymphoid tissue (e.g. germinal centers). Therefore, "anti-CXCL13 activity" or "CXCL13 blocking activity" can include activity which modulates one or more of the following activities associated with CXCL13: blockade of CXCL13 interaction with its receptor, inhibition of B cell and follicular B-helper T cell migration into inflamed tissues, inhibition of germinal center formation (e.g., in the case of autoimmune diseases), inhibition of secondary or ectopic lymphoid follicles; inhibition of cancer cell proliferation and ability to spread in oncological disorders; or any other activity associated with CXCL13-expressing cells. Anti-CXCL13 activity can also be attributed to a decrease in incidence or severity of diseases associated with CXCL13 expression, including, but not limited to, certain types of autoimmune diseases (e.g., multiple sclerosis, arthritis (e.g., rheumatoid arthritis), chronic gastritis, gastric lymphomas, transplant rejection, Sjogren's Syndrome (SS), systemic lupus erythematosus (SLE), active mixed cryoglobulinemia (MC) vasculitis in Hepatitis C virus infection, juvenile dermatomyositis, and myasthenia gravis) and certain cancers (e.g., Burkitt's lymphoma, non-Hodgkin lymphoma, MALT lymphoma (e.g., gastric MALT lymphoma), carcinoma (e.g., colon, prostate, breast, stomach, esophageal, and pancreatic), and chronic lymphocytic leukemia (CLL)) as well as other inflammatory diseases such as *Helicobacter* infection induced inflammatory diseases, e.g., gastritis, ulcers, and gastric mucosal lesions.

When discussed herein whether any particular polypeptide, including the constant regions, CDRs, VH domains, or VL domains of a reference polypeptide, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-CXCL13 antibody (e.g., MAb 5261, MAb 5378, MAb 5080, MAb 1476, or 3D2) or anti-CXCR5 antibody by as few as 1 to 15 amino acid residues, as few as 1 to 10 amino acid residues, such as 6-10, as few as 5, as few as 4, 3, 2, or even 1 amino acid residue.

The precise chemical structure of a polypeptide capable of specifically binding CXCL13 or CXCR5 and retaining the desired CXCL13 blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-CXCL13 or anti-CXCR5 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CXCL13 or anti-CXCR5 antibody used herein so long as the desired properties of the anti-CXCL13 or anti-CXCR5 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for CXCL13 or CXCR5, binding affinity, and/or CXCL13 blocking activity) do not remove the polypeptide sequence from the definition of anti-CXCL13 or anti-CXCR5 antibodies of interest as used herein.

The art provides substantial guidance regarding the preparation and use of polypeptide variants. In preparing the anti-CXCL13 or anti-CXCR5 binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present invention.

The constant region of a reference anti-CXCL13 or anti-CXCR5 antibody may be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-CXCL13 or anti-CXCR5 antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

In general, CXCR5 binding molecules useful in the presently disclosed methods do not activate the CXCR5 receptor (i.e., are not agonists of the receptor).

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., binding specificity for CXCL13 or CXCR5, binding affinity, and/or CXCL13 blocking activity).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a CXCL13 or CXCR5 polypeptide) can be determined using techniques described herein or by routinely modifying techniques known in the art.

In certain embodiments, the anti-CXCL13 or anti-CXCR5 antibodies useful in the presently disclosed methods comprise at least one optimized complementarity-determining region (CDR) in comparison to a reference anti-CXCL13 or anti-CXCR5 antibody. By "optimized CDR" is intended that the CDR has been modified and optimized sequences selected based on the sustained or improved binding affinity and/or anti-CXCL13 activity that is imparted to an anti-CXCL13 or anti-CXCR5 antibody comprising the optimized CDR.

As discussed in more detail elsewhere herein, anti-CXCL13 or anti-CXCR5 binding molecules, or soluble CXCR5 may further be recombinantly fused to a heterologous polypeptide at the N- or C-terminus or chemically conjugated (including covalent and non-covalent conjugations) to polypeptides or other compositions. For example, anti-CXCL13 or anti-CXCR5 antibodies or soluble CXCR5 may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

Anti-CXCL13 or anti-CXCR5 antibodies useful in the presently disclosed methods may include derivatives that are modified, i.e., by the covalent attachment of any type of molecule to the antibody such that covalent attachment does not prevent the antibody binding CXCL13 or CXCR5. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-CXCL13 or anti-CXCR5 binding molecules, e.g., antibodies, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-CXCL13 or anti-CXCR5 antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-CXCL13 or anti-CXCR5 binding molecule, including the peptide backbone, the amino acid side-chains and the amino or carboxyl termini, or on moieties such as carbohydrates. It will be appreciated that the same type of modification may be present in the same or varying degrees at several sites in a given anti-CXCL13 or anti-CXCR5 binding molecule. Also, a given anti-CXCL13 or anti-CXCR5 binding molecule may contain many types of modifications. Anti-CXCL13 or anti-CXCR5 binding molecules may be branched, for example, as a result of ubiquitination, and they may be cyclic, with or without branching. Cyclic, branched, and branched cyclic anti-CXCL13 or anti-CXCR5 binding molecules may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Posttranslational Covalent Modification of Proteins (Academic Press, NY), pgs. 1-12; Seifter et al., Meth. Enzymol. 182:626-646 (1990); Rattan et al., Ann. NY Acad. Sci. 663:48-62 (1992)).

The presently disclosed methods encompass the use of fusion proteins comprising an anti-CXCL13 or anti-CXCR5 antibody, or antigen-binding fragment, variant, or derivative thereof, and a heterologous polypeptide. The heterologous polypeptide to which the antibody is fused may be useful for function or is useful to target the anti-CXCL13 or anti-CXCR5 polypeptide expressing cells.

In one embodiment, a fusion protein useful in the presently disclosed methods comprises, consists essentially of, or consists of, a polypeptide having the amino acid sequence of any one or more of the VH domains of an anti-CXCL13 or anti-CXCR5 antibody or the amino acid sequence of any one or more of the VL domains of an anti-CXCL13 or anti-CXCR5 antibody or fragments or variants thereof, and a heterologous polypeptide sequence.

In another embodiment, a fusion protein for use in the treatment methods disclosed herein comprises, consists essentially of, or consists of a polypeptide having the amino acid sequence of any one, two, three of the CDRs of the VH domain of an anti-CXCL13 or anti-CXCR5 antibody, or fragments, variants, or derivatives thereof, and/or the amino acid sequence of any one, two, three of the CDRs of the VL domain an anti-CXCL13 or anti-CXCR5 antibody, or fragments, variants, or derivatives thereof, and a heterologous polypeptide sequence. In some embodiments, the VH and VL domains of the fusion protein correspond to a single source antibody (or scFv or Fab fragment) that specifically binds at least one epitope of CXCL13 or CXCR5. In some embodiments, two, three, four, five, six, or more of the CDR(s) of the VH domain or VL domain correspond to single source antibody (or scFv or Fab fragment).

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349:164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

As discussed elsewhere herein, anti-CXCL13 or anti-CXCR5 binding molecules, e.g., antibodies, or antigen-binding fragments, variants, or derivatives thereof, may be fused to heterologous polypeptides to increase the in vivo half life of the polypeptides or for use in immunoassays using methods known in the art. For example, in one embodiment, PEG can be conjugated to the anti-CXCL13 or anti-CXCR5 antibodies to increase their half-life in vivo. See Leong et al., Cytokine 16:106 (2001); Adv. in Drug Deliv. Rev. 54:531 (2002); or Weir et al., Biochem. Soc. Transactions 30:512 (2002).

Moreover, anti-CXCL13 or anti-CXCR5 binding molecules, e.g., antibodies, or antigen-binding fragments, variants, or derivatives thereof, can be fused to marker sequences, such as a peptide to facilitate their purification or detection. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Anti-CXCL13 and anti-CXCR5 binding molecules, e.g., antibodies, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-CXCL13 or anti-CXCR5 binding molecules, e.g., antibodies, or antigen-binding fragments, variants, or derivatives thereof, can be labeled or conjugated either before or after purification, or when purification is performed.

In particular, anti-CXCL13 or anti-CXCR5 antibodies, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of anti-CXCL13 or anti-CXCR5 antibodies, or antigen-binding fragments, variants, or derivatives thereof, are prepared in an analogous manner.

An anti-CXCL13 or anti-CXCR5 binding molecule, e.g., an antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells.

Techniques for conjugating various moieties to an antibody, e.g., an anti-CXCL13 or anti-CXCR5 antibody or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R Liss, Inc.), pp. 243-56; Hellstrom et al. (1987) "Antibodies for Drug Delivery," in Controlled Drug Delivery, ed. Robinson et al. (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al., *Immunol. Rev.* 62:119-58 (1982).

Methods of preparing and administering the agent that inhibits CXCL13 activity (e.g., an anti-CXCL13 or anti-CXCR5 binding molecule) to a subject in need thereof are well known to or are readily determined by those skilled in the art. The route of administration of the agent that inhibits CXCL13 activity (e.g., an anti-CXCL13 or anti-CXCR5 binding molecule) may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, agents that inhibit CXCL13 activity (e.g., anti-CXCL13 or anti-CXCR5 binding molecules) can be delivered directly to the site of the adverse cellular population thereby increasing the exposure of the diseased tissue to the therapeutic agent.

As discussed herein, agents that inhibit CXCL13 activity (e.g., anti-CXCL13 or anti-CXCR5 binding molecules) may be administered in a pharmaceutically effective amount for the in vivo treatment of inflammatory disorders and for increasing levels of IgA. In this regard, it will be appreciated that the agents that inhibit CXCL13 activity will be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an agent that inhibits CXCL13 activity (e.g., anti-CXCL13 or anti-CXCR5 binding molecule) shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M, e.g., 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In certain cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-CXCL13 or anti-CXCR5 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an agent that inhibits CXCL13 activity (e.g., anti-CXCL13 or anti-CXCR5 binding molecule) that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, an agent that inhibits CXCL13 activity (e.g., anti-CXCL13 antibodies, or antigen-binding fragments, variants, or derivatives thereof) may be administered to a human or other animal in accordance with the aforementioned methods of treatment in an amount sufficient to produce a therapeutic effect. The agent that inhibits CXCL13 activity (e.g., anti-CXCL13 or anti-CXCR5 antibodies, or antigen-binding fragments, variants, or derivatives thereof can be administered to such human or other animal in a conventional dosage form prepared by combining the active agent with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of agents that inhibit CXCL13 activity (e.g., anti-CXCL13 or anti-CXCR5 binding molecules) may prove to be particularly effective.

By "therapeutically effective dose or amount" or "effective amount" is intended an amount of an agent that inhibits CXCL13 activity (e.g., anti-CXCL13 or anti-CXCR5 binding molecule), that when administered brings about a positive therapeutic response with respect to treatment of a patient with a disease to be treated.

Therapeutically effective doses of agents that inhibit CXCL13 activity for treatment of inflammatory disorders and for increasing IgA levels vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one agent that inhibits CXCL13 activity (e.g., anti-CXCL13 or anti-CXCR5 binding molecule) to be administered is readily determined by one of ordinary skill in the art without undue experimentation given the disclosure of the present invention. Factors influencing the mode of administration and the respective amount of at least one agent that inhibits CXCL13 activity (e.g., anti-CXCL13 or anti-CXCR5 binding molecule) include, but are not limited to, the severity of the disease, the history of the disease, and the age, height, weight, health, and physical condition of the individual undergoing therapy. Similarly, the amount of an agent that inhibits CXCL13 activity (e.g., anti-CXCL13 or anti-CXCR5 binding molecule) to be administered will be dependent upon the mode of administration and whether the subject will undergo a single dose or multiple doses of this agent.

In some embodiments, the dosage of an agent that inhibits CXCL13 activity (e.g., anti-CXCL13 or anti-CXCR5 binding molecule) that is administered ranges from about 0.1 mg/kg to about 100 mg/kg, including but not limited to about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, and about 10 mg/kg. In certain embodiments, the dosage that is administered ranges from about 1 mg/kg to about 10 mg/kg. In particular embodiments, about 4 mg/kg to about 5 mg/kg of an agent that inhibits CXCL13 activity (e.g., anti-CXCL13 or anti-CXCR5 binding molecule) is administered to a subject in need thereof. In some of these embodiments, the agent is administered via intraperitoneal injection.

The present invention also provides for the use of an agent that inhibits CXCL13 activity (e.g., anti-CXCL13 or anti-CXCR5 binding molecule) in the manufacture of a medicament for treating an inflammatory disorder and for increasing IgA levels.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hal12003); Harlow and Lane (1988) Antibodies: A Laboratory Manual (Cold Spring Harbor Press); Dieffenbach and Dveksler (2003) PCR Primer (Cold Spring Harbor Press).

It is to be noted that the term "a" or "an" entity refers to one or more of that entity; for example, "an anti-CXCL13 antibody" is understood to represent one or more anti-CXCL13 antibodies. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller ranges is also encompassed within the invention, subject to any specifically excluded limit in the stated range. Where the stated range includes one or both of the limits, ranges excluding either or both of those included limits are also included in the invention.

The following examples are offered by way of illustration and not by way of limitation.

EXPERIMENTAL

Example 1. Evaluation of Anti-CXCL13 Antibodies in a Mouse Model for *Helicobacter* Infection Murine Model of *Helicobacter* Infection.

*Heliobacter* species such as *H. heilmannii* and *H. Pylori* induce gastric MALT lymphoma in patients. A mouse model of *Heliobacter* induced gastric lymphoid follicles was described in Nobutani et al. (2010) *FEMS Immunol Med Microbiol* 60:156-164, which is incorporated herein by reference in its entirety. The Nobutani et al. mouse model was used herein to test the effect of anti-CXCL13 antibody in reducing infectious burden, by which is meant the titer of bacteria, in that tissue. C57BL/6J mice (n=5) were orally infected with *H. suis*. Starting one week post-infection, the mice received 0.6 mg i.p. of either isotype antibody control (MAb 2510) or anti-CXCL13 antibody (MAb 5378) weekly for twelve weeks.

Twelve weeks after *H. suis* infection, the mice were sacrificed. Gastric samples from the mice were evaluated by PCR for expression of *H. suis* specific 16s rRNA genes as a measure of the relative level of infection with *H. suis*. The *H. suis* specific 16s rRNA gene PCR primers are shown below:

```
                                         (SEQ ID NO: 22)
F: 5'-TTGGGAGGCTTTGTCTTTCCA-3'

(SEQ ID NO: 23)
R: 5'-GATTAGCTCTGCCTCGCGGCT-3'
```

PCR amplification reactions involved 1× reaction buffer [20 mM Tris/HCl (pH8.0), 100 mM KCl, 0.1 mM EDTA, 1 mM DTT, 0.5% Tween-20, 0.5% Nonidet P40, and 50% glycerol] containing 1 unit of Taq DNA polymerase (TOYOBO, Osaka, Japan); 10 nmols of each deoxynucleotide triphosphate; 10 pmols of each oligonucleotide primer; and 1 μl of the diluted DNA, which was prepared by 1:10 dilution of the original samples with a DNA concentration of approximately 20-100 ng/μl, in a final volume of 50 μl. Cycling conditions for the 16s rRNA reactions involved 35 cycles of 94° C. for 30 seconds, 56° C. for 30 seconds, and 72° C. for 30 seconds.

Anti-CXCL13 Antibody Reduces Titers of *Helicobacter* Infected Mice.

The relative number of *H. suis* in the gastric mucosa of *H. suis* infected mice treated with anti-CXCL13 antibody or isotype control antibody was determined by real-time quantitative PCR. These results in FIG. 1 show a decrease in titers of *H. suis* in stomachs of infected mice treated with anti-CXCL13 antibody.

Anti-CXCL13 Antibody Induces TGF-β and IL-6 in Gastric Lymphoid Follicles of *H. suis* Infected Mice.

The mRNA expression levels of TGF-β and IL-6 mRNA in the gastric mucosa of H. suis infected mice after treatment with isotype control or anti-CXCL13 antibody (mAb 5378) was determined by reverse transcription PCR. The mucosal and submucosal layers of the stomach were removed from the muscularis and serosa, and then homogenized with 1 ml of TRIZOL Reagent (Invitrogen). RNA was extracted from the homogenates according to the manufacturer's instructions. RNA was subjected to the reverse transcription reaction using a High Capacity cDNA Reverse Transcription Kit (Applied Biosystems, Foster City, Calif.) according to the manufacturer's protocol, and quantitative PCR was performed using Power SYBR Green PCR Master Mix (Applied Biosystems) according to the manufacturer's instructions. To allow a relative comparison of RNA expression levels, the data from quantitative PCR were normalized to the amount of β-actin cDNA as an endogenous control. Specific primer pairs (Hokkaido System Science Co. Ltd., Sapporo, Japan) used for quantitative PCR were as follows:

```
TGF-β sense
                              (SEQ ID NO: 24)
5'-TCTTGGTCCAGATCACAACTTCA-3'

TGF-β antisense
                              (SEQ ID NO: 25)
5'-CACTGATACGCCTGAGTGR-3'

IL-6 sense
                              (SEQ ID NO: 26)
5'-GTGAGCGCTGAATCGAAA-3'

IL-6 antisense
                              (SEQ ID NO: 27)
5'-GAGGATACCACTCCCAACAGACC-3'

β-actin sense
                              (SEQ ID NO: 28)
5'-ATCACTGACGCTGATTGCAC-3'

β-actin antisense
                              (SEQ ID NO: 29)
5'-AAGGCCAACCGTGAAAAGAT-3'
```

Quantitative real-time PCR involved homogenizing the mucosal and submucosal layers of the stomach with 1 ml of TRIZOL Reagent (Invitrogen) and extracting RNA from the homogenates according to the manufacturer's instructions. RNA was then subjected to the reverse transcription reaction using a High Capacity cDNA Reverse Transcription Kit (Applied Biosciences, Foster City, Calif.) according to the manufacturer's instructions, and quantitative real-time PCR was performed using Power SYBR Green PCR Master Mix (Applied Biosciences, Foster City, Calif.) and ABI Prism 7500 Real Time PCR System (Applied Biosciences, Foster City, Calif.) according to the manufacturer's instructions. To allow a relative comparison of RNA expression levels, the data from real-time PCR were normalized to the amount of β-actin cDNA as an endogenous control.

Figure 2A:
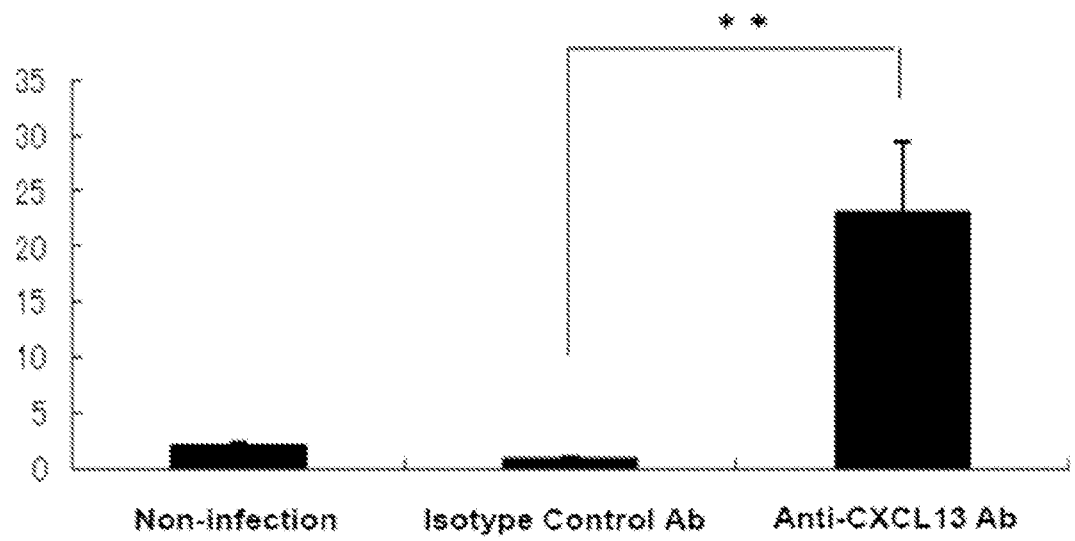
FIGS. 2A and 2B show the expression of TGF-β (FIG. 2A) and IL-6 (FIG. 2B) mRNA in the stomach of *H. suis* infected mice after isotype control or anti-CXCL13 antibody treatment.
Figure 2B:
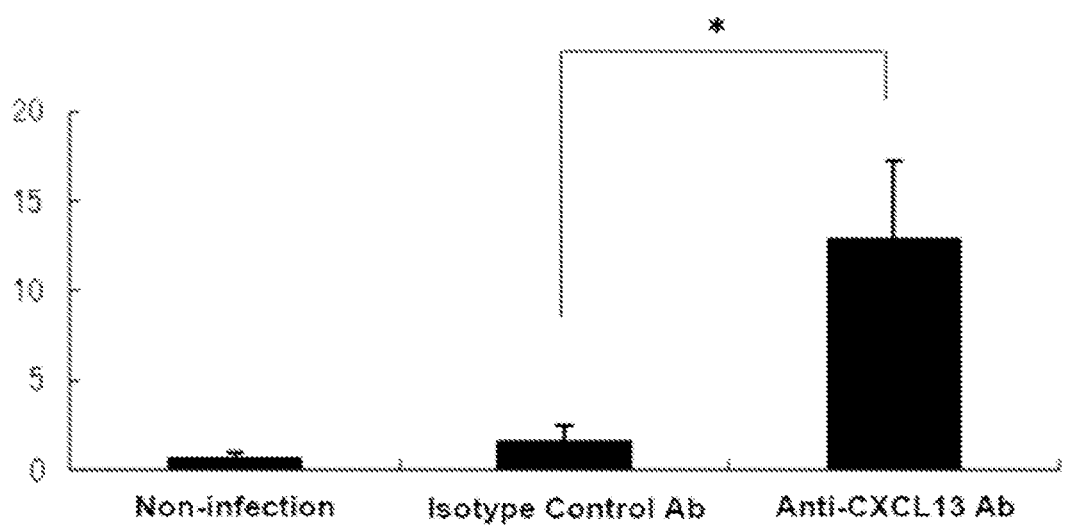

FIGS. 2A and 2B show the expression of TGF-β and IL-6 mRNA, respectively, in the stomach of H. suis infected mice after isotype control or anti-CXCL13 antibody (MAb 5378) treatment. These results show a significant increase in the expression of both TGF-β and IL-6 mRNA in H. suis infected mice treated with an anti-CXCL13 antibody as compared to mice treated with isotype control and uninfected mice. Interestingly, the expression levels of TGF-β and IL-6 in the stomachs of uninfected mice were also significantly induced by treatment with anti-CXCL13 antibodies (MAb 5378) (data not shown).

Because TGF-β and IL-6 can increase expression of IgA, these results suggested that H. suis specific IgA may be upregulated by anti-CXCL13 antibody treatment in the H. suis infected mouse stomachs. Thus, the treatment of H. suis infected mice with anti-CXCL13 antibody might lead to the inhibition of H. suis colonization via inducing H. suis specific IgA through the activation of TGF-β and IL-6 dependent pathways.

Anti-CXCL13 Antibody Treatment Increases IgA Secretion in Gastric Lymphoid Follicles in Helicobacter Infected Mice.

The stomachs of mice three months after H. suis infection were resected and opened at the greater curvature Immunofluorescence staining of stomach samples from noninfected wild-type mice, isotype control and anti-CXCL13 antibody (MAb 5378) treated mice for IgA and actin (data not shown) showed an increase in IgA secretion in the gastric lymphoid follicles in H. suis infected mice treated with anti-CXCL13 antibody compared to control treatment.

Levels of Anti-H. suis Specific IgG and IgA in the Serum and Gastric Juice of Mice after H. suis Infection.

To detect H. suis specific IgG in the serum and gastric juice, the gastric juice was centrifuged at 16,000×g for 5 min at 4° C., and the resultant supernatant was collected. The serum was separated from the blood by centrifugation at 15,000×g for 10 min at 4° C. Ninety six-well plates were coated overnight at 4° C. with 100 μl of a bicarbonate solution (pH 9.6) containing 100 μg/ml H. pylori lysate, and blocked by the addition of 1.5% (wt/vol) BSA in PBS for 1 h at 37° C. The serum and gastric juice, which were diluted at 1:200 and 1:15, respectively, were added to the plates, followed by addition of 100 μl of HRP-conjugated goat anti-mouse IgG antibody (Bio-Rad Laboratories, Hercules, Calif.) diluted at 1:5.000 in PBST containing 0.2% (wt/vol) BSA and anti-mouse IgA. The bound antibody was detected by addition of o-phenylenediamine substrate, and measurement of absorbance at 490 nm was carried out.

Figure 3A:
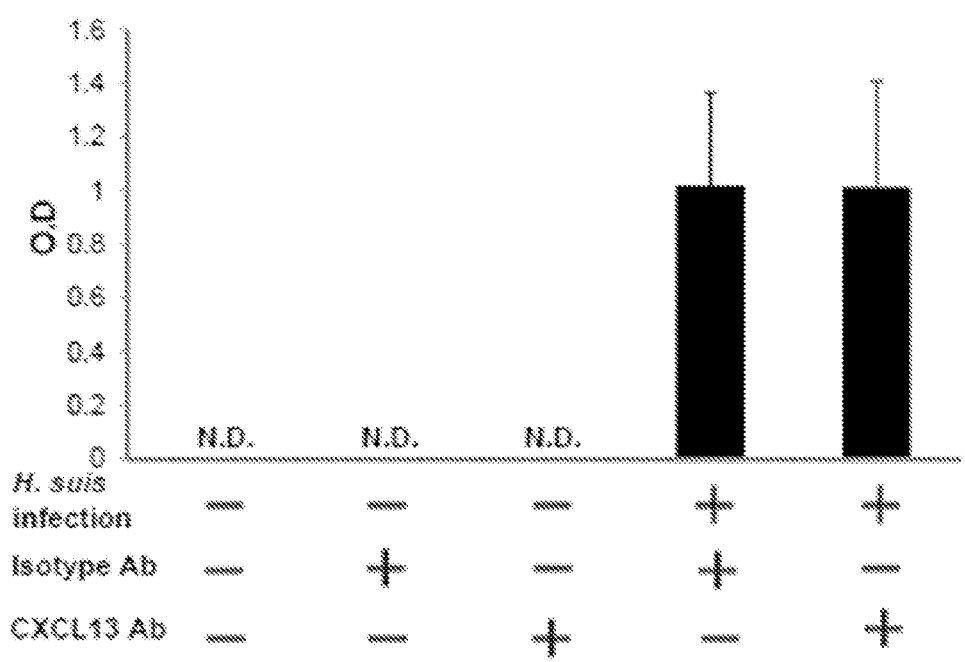
FIGS. 3A and 3B show serum levels of anti-*H. suis* IgG (FIG. 3A) and IgA (FIG. 3B) of *H. suis* infected mice treated with anti-CXCL13 antibody or isotype control antibody.
Figure 3B:
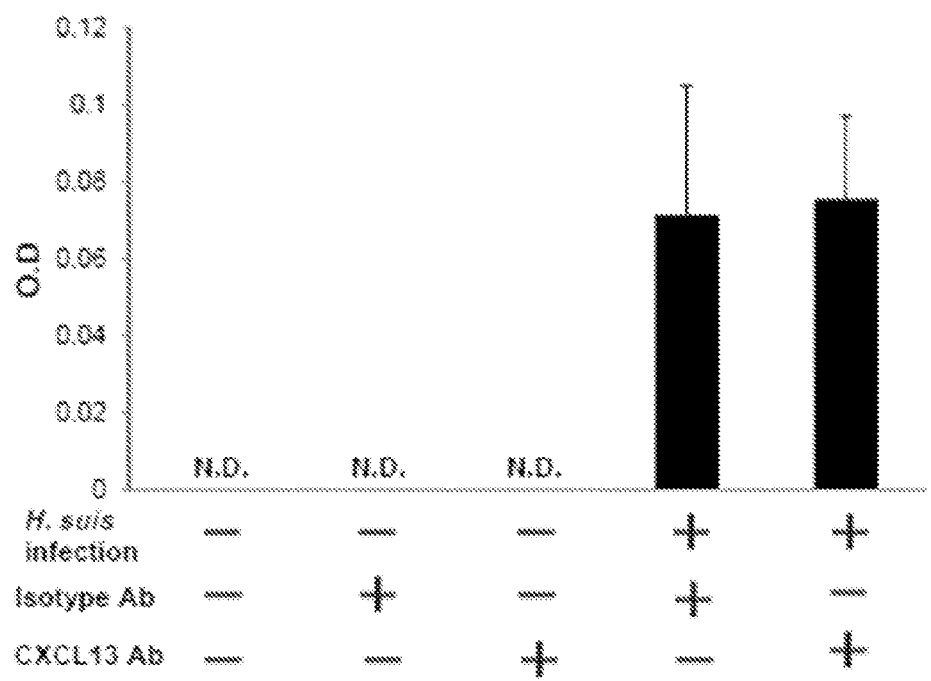
Figure 4A:
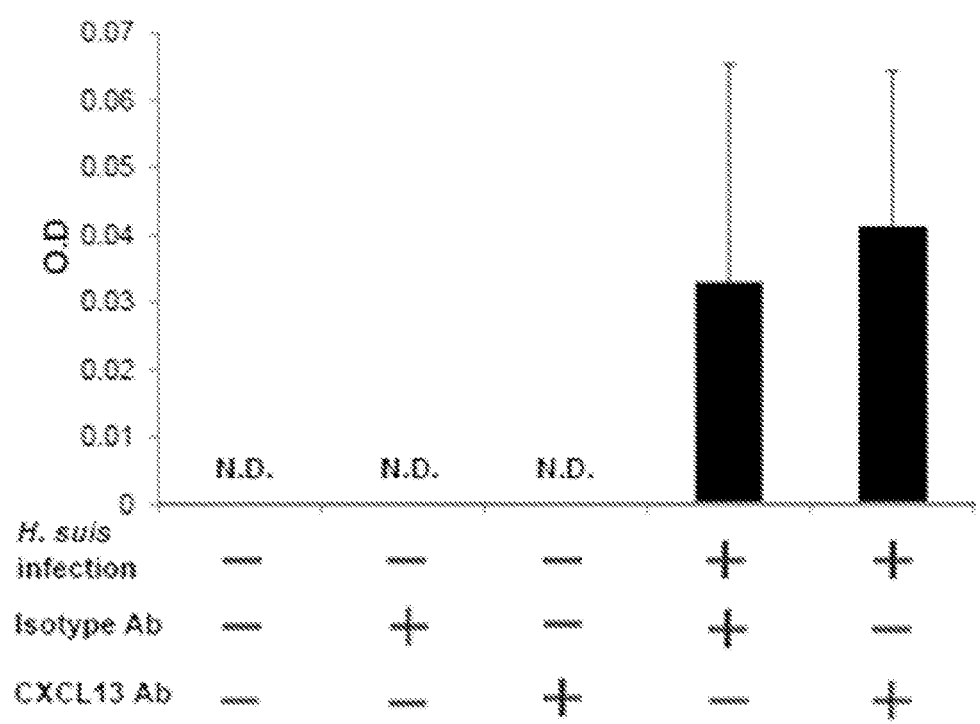
FIGS. 4A and 4B show levels of anti-*H. suis* IgG (FIG. 4A) and IgA (FIG. 4B) in the gastric juice of *H. suis* infected mice treated with anti-CXCL13 antibody or isotype control antibody.
Figure 4B:
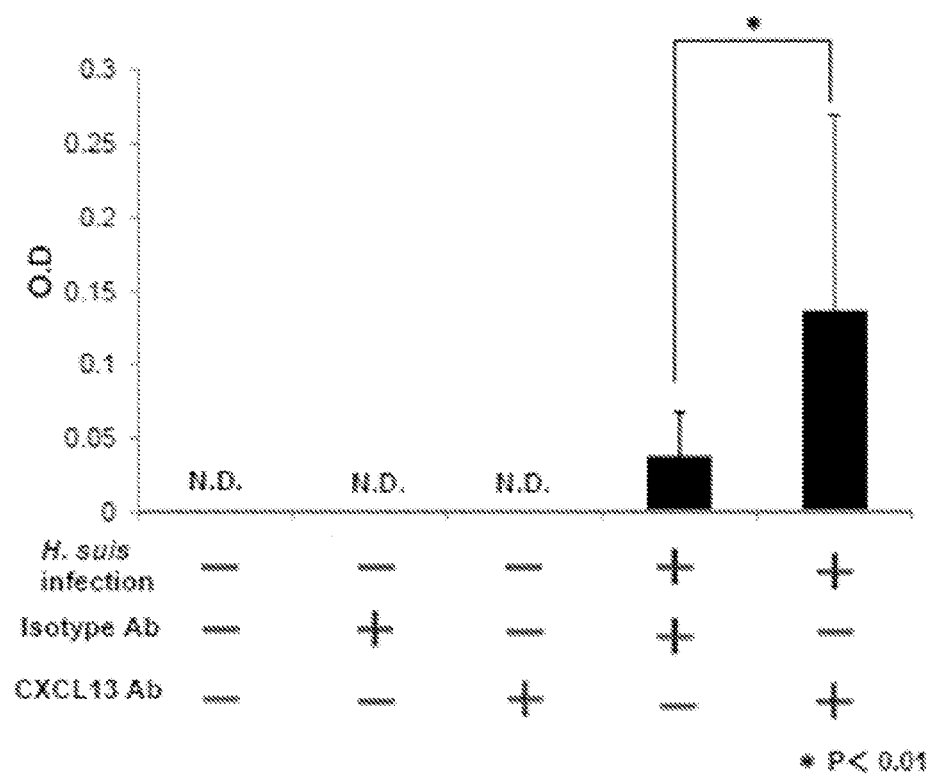

Levels of anti-H. suis specific IgG and IgA in the serum and gastric juice of H. suis infected mice were measured. FIGS. 3A and 4A show that while anti-H. suis specific IgG is induced in serum and gastric juice by H. suis infection, there were no differences in the levels of anti-H. suis specific IgG in the serum or the gastric juice of anti-CXCL13 antibody (MAb 5378) and isotype control antibody treated mice. FIGS. 3B and 4B show that anti-H. suis specific IgA is induced in the serum and gastric juice by H. suis infection. While there are no significant differences in the levels of anti-H. suis specific IgA in the serum of anti-CXCL13 antibody and isotype control antibody treated mice, levels of anti-H. suis specific IgA are significantly higher in the gastric juice of the anti-CXCL13 antibody compared to the isotype control antibody treated mice. These results demonstrate that inhibition of CXCL13 produced by inflammatory cells of infected tissue results in an increase in IgA specific for the infectious agent and is associated with enhanced clearance of that bacterial infection.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method for increasing immunoglobulin A (IgA) levels in a subject having a deficiency thereof, said method comprising administering to said subject an effective amount of an antibody or antigen-binding fragment thereof that specifically binds CXCL13 and inhibits CXCL13 activity, wherein the antibody or antigen-binding fragment thereof
   a) comprises a variable heavy (VH) domain having three complementarity determining regions (CDRs) of SEQ ID NO: 10 and a variable light (VL) domain having three CDRs of SEQ ID NO: 15;
   b) comprises a variable heavy (VH) domain having three complementarity determining regions (CDRs) of SEQ ID NO: 14 and a variable light (VL) domain having three CDRs of SEQ ID NO: 19; or
   c) comprises a variable heavy (VH) domain having three complementarity determining regions (CDRs) of SEQ ID NO: 14 and a variable light (VL) domain having three CDRs of SEQ ID NO: 21.

2. The method of claim 1, wherein said IgA deficiency is secondary to an infection or exposure to a drug.

3. The method of claim 2, wherein said infection is a mucosal infection.

4. The method of claim 2, wherein said infection is a bacterial infection.

5. The method of claim 4, wherein said bacterial infection is a *Helicobacter* infection.

6. The method of claim 5, wherein said *Helicobacter* is selected from the group consisting of *Helicobacter pylori*, *Helicobacter heilmannii*, and *Helicobacter suis*.

7. The method of claim 1, wherein said IgA deficiency is a primary IgA deficiency.

8. The method of claim 1, wherein secretory IgA levels are increased in said subject upon administration of said antibody or antigen-binding fragment thereof.

9. The method of claim 8, wherein gastric IgA levels are increased in said subject upon administration of said antibody or antigen-binding fragment thereof.

10. The method of claim 1, wherein said method increases IgA antibody responses in a mucosal tissue of said subject.

11. The method of claim 1, wherein said antibody is chimeric, human, or humanized.

12. The method of claim 1, wherein said antibody is selected from the group consisting of MAb 5261, MAb 5378, MAb 5080, MAb 1476, and MAb 3D2.

13. The method of claim 1, wherein said antibody or antigen-binding fragment thereof inhibits the interaction of CXCL13 with a CXCL13 receptor.

14. The method of claim 13, wherein said CXCL13 receptor is CXCR5.

15. The method of claim 1, wherein said antibody or antigen-binding fragment thereof inhibits CXCR5 receptor internalization.

16. The method of claim 1, wherein said antibody or antigen-binding fragment thereof is administered with a pharmaceutically acceptable carrier.

17. The method of claim 1, wherein said subject is an animal.

18. The method of claim 17, wherein said animal is a mammal.

19. The method of claim 18, wherein said mammal is a human.

20. The method of claim 1, wherein the VH domain of said antibody or antigen-binding fragment thereof comprises a CDR1 comprising amino acid residues 31-35 of SEQ ID NO: 10, a CDR2 comprising amino acid residues 50-65 of SEQ ID NO: 10, and a CDR3 comprising amino acid residues 95-102 of SEQ ID NO: 10, and the VL domain of said antibody or antigen-binding fragment thereof comprises a CDR1 comprising amino acid residues 24-34 of SEQ ID NO: 15, a CDR2 comprising amino acid residues 50-56 of SEQ ID NO: 15, and a CDR3 comprising amino acid residues 89-97 of SEQ ID NO: 15, wherein the CDR residues are numbered according to Kabat.

21. The method of claim 1, wherein the VH domain of said antibody or antigen-binding fragment thereof comprises a CDR1 comprising amino acid residues 26-32 of SEQ ID NO: 10, a CDR2 comprising amino acid residues 52-58 of SEQ ID NO: 10, and a CDR3 comprising amino acid residues 95-102 of SEQ ID NO: 10, and the VL domain of said antibody or antigen-binding fragment thereof comprises a CDR1 comprising amino acid residues 26-32 of SEQ ID NO: 15, a CDR2 comprising amino acid residues 50-52 of SEQ ID NO: 15, and a CDR3 comprising amino acid residues 91-96 of SEQ ID NO: 15, wherein the CDR residues are numbered according to Chothia.

22. The method of claim 1, wherein the VH domain of said antibody or antigen-binding fragment thereof has the amino acid sequence set forth as SEQ ID NO: 10 and the VL domain of said antibody or antigen-binding fragment thereof has the amino acid sequence set forth as SEQ ID NO: 15.

23. The method of claim 1, wherein the VH domain of said antibody or antigen-binding fragment thereof comprises a CDR1 comprising amino acid residues 31-35 of SEQ ID NO: 14, a CDR2 comprising amino acid residues 50-65 of SEQ ID NO: 14, and a CDR3 comprising amino acid residues 95-102 of SEQ ID NO: 14, and the VL domain of said antibody or antigen-binding fragment thereof comprises a CDR1 comprising amino acid residues 24-34 of SEQ ID NO: 19, a CDR2 comprising amino acid residues 50-56 of SEQ ID NO: 19, and a CDR3 comprising amino acid residues 89-97 of SEQ ID NO: 19, wherein the CDR residues are numbered according to, according to Kabat.

24. The method of claim 1, wherein the VH domain of said antibody or antigen-binding fragment thereof comprises a CDR1 comprising amino acid residues 26-32 of SEQ ID NO: 14, a CDR2 comprising amino acid residues 52-58 of SEQ ID NO: 14, and a CDR3 comprising amino acid residues 95-102 of SEQ ID NO: 14, and the VL domain of said antibody or antigen-binding fragment thereof comprises a CDR1 comprising amino acid residues 26-32 of SEQ ID NO: 19, a CDR2 comprising amino acid residues 50-52 of SEQ ID NO: 19, and a CDR3 comprising amino acid residues 91-96 of SEQ ID NO: 19, wherein the CDR residues are numbered according to Chothia.

25. The method of claim 1, wherein the VH domain of said antibody or antigen-binding fragment thereof has the amino acid sequence set forth as SEQ ID NO: 14 and the VL domain of said antibody or antigen-binding fragment thereof has the amino acid sequence set forth as SEQ ID NO: 19.

26. The method of claim 1, wherein the VH domain of said antibody or antigen-binding fragment thereof comprises a CDR1 comprising amino acid residues 31-35 of SEQ ID NO: 14, a CDR2 comprising amino acid residues 50-65 of SEQ ID NO: 14, and a CDR3 comprising amino acid residues 95-102 of SEQ ID NO: 14, and the VL domain of said antibody or antigen-binding fragment thereof comprises a CDR1 comprising amino acid residues 24-34 of SEQ ID NO: 21, a CDR2 comprising amino acid residues 50-56 of SEQ ID NO: 21, and a CDR3 comprising amino acid residues 89-97 of SEQ ID NO: 21, wherein the CDR residues are numbered according to Kabat.

27. The method of claim 1, wherein the VH domain of said antibody or antigen-binding fragment thereof comprises a CDR1 comprising amino acid residues 26-32 of SEQ ID NO: 14, a CDR2 comprising amino acid residues 52-58 of SEQ ID NO: 14, and a CDR3 comprising amino acid residues 95-102 of SEQ ID NO: 14, and the VL domain of said antibody or antigen-binding fragment thereof comprises a CDR1 comprising amino acid residues 26-32 of SEQ ID NO: 21, a CDR2 comprising amino acid residues 50-52 of SEQ ID NO: 21, and a CDR3 comprising amino acid residues 91-96 of SEQ ID NO: 21, wherein the CDR residues are numbered according to Chothia.

28. The method of claim 1, wherein the VH domain of said antibody or antigen-binding fragment thereof has the amino acid sequence set forth as SEQ ID NO: 14 and the VL domain of said antibody or antigen-binding fragment thereof has the amino acid sequence set forth as SEQ ID NO: 21.

29. The method of claim 1, wherein said antibody or antigen-binding fragment thereof comprises a variable heavy (VH) domain comprising a CDR1 having the sequence set forth in SEQ ID NO: 11, a CDR2 having the sequence set forth in SEQ ID NO: 12, and a CDR3 having the sequence set forth in SEQ ID NO: 13; and a variable light (VL) domain comprising a CDR1 having the sequence set forth in SEQ ID NO: 16 or 20, a CDR2 having the sequence set forth in SEQ ID NO: 17, and a CDR3 having the sequence set forth in SEQ ID NO: 18.

30. The method of claim 29, wherein said CDR1 of said VL domain has the sequence set forth in SEQ ID NO: 20.

* * * * *

SEQUENCE LISTING

```
<160> NUMBER OF SEQ ID NOS: 29

<210> SEQ ID NO 1
<211> LENGTH: 1201
<212> TYPE: DNA
<213> ORGANISM: Homo sapiens
<220> FEATURE:
<221> NAME/KEY: CDS
<222> LOCATION: (79)...(408)

<400> SEQUENCE: 1
gagaagatgt ttgaaaaaac tgactctgct aatgagcctg gactcagagc tcaagtctga        60
actctacctc cagacaga atg aag ttc atc tcg aca tct ctg ctt ctc atg       111
                    Met Lys Phe Ile Ser Thr Ser Leu Leu Leu Met
                      1               5                  10 ctg ctg gtc agc agc ctc tct cca gtc caa ggt gtt ctg gag gtc tat       159
Leu Leu Val Ser Ser Leu Ser Pro Val Gln Gly Val Leu Glu Val Tyr
            15                  20                  25 tac aca agc ttg agg tgt aga tgt gtc caa gag agc tca gtc ttt atc       207
Tyr Thr Ser Leu Arg Cys Arg Cys Val Gln Glu Ser Ser Val Phe Ile
        30                  35                  40 cct aga cgc ttc att gat cga att caa atc ttg ccc cgt ggg aat ggt       255
Pro Arg Arg Phe Ile Asp Arg Ile Gln Ile Leu Pro Arg Gly Asn Gly
    45                  50                  55 tgt cca aga aaa gaa atc ata gtc tgg aag aag aac aag tca att gtg       303
Cys Pro Arg Lys Glu Ile Ile Val Trp Lys Lys Asn Lys Ser Ile Val
60                  65                  70                  75 tgt gtg gac cct caa gct gaa tgg ata caa aga atg atg gaa gta ttg       351
Cys Val Asp Pro Gln Ala Glu Trp Ile Gln Arg Met Met Glu Val Leu
                80                  85                  90 aga aaa aga agt tct tca act cta cca gtt cca gtg ttt aag aga aag       399
Arg Lys Arg Ser Ser Ser Thr Leu Pro Val Pro Val Phe Lys Arg Lys
                95                 100                 105 att ccc tga tgctgatatt tccactaaga acacctgcat tcttcccta                 448
Ile Pro tccctgctct ggatttagt tttgtgctta gttaaatctt ttccaggaaa aagaacttcc       508
ccatacaaat aagcatgaga ctatgtaaaa ataaccttgc agaagctgat ggggcaaact       568
caagcttctt cactcacagc accctatata cacttggagt ttgcattctt attcatcagg       628
gaggaaagtt tctttgaaaa tagttattca gttataagta atacaggatt atttttgatta      688 tatacttgtt gtttaatgtt taaaatttct tagaaaacaa tggaatgaga atttaagcct       748
caaatttgaa catgtggctt gaattaagaa gaaaattatg gcatatatta aaagcaggct       808
tctatgaaag actcaaaaag ctgcctggga ggcagatgga acttgagcct gtcaagaggc       868
aaaggaatcc atgtagtaga tatcctctgc ttaaaaactc actacggagg agaattaagt       928 cctacttta aagaatttct ttataaaatt tactgtctaa gattaatagc attcgaagat        988
```

-continued

```
ccccagactt catagaatac tcagggaaag catttaaagg gtgatgtaca catgtatcct      1048
ttcacacatt tgccttgaca aacttctttc actcacatct tttcactga cttttttgt       1108 gggggcggg gccgggggga ctctggtatc taattcttta atgattccta taaatctaat      1168
gacattcaat aaagttgagc aaacatttta ctt                                  1201
```

<210> SEQ ID NO 2
<211> LENGTH: 109
<212> TYPE: PRT
<213> ORGANISM: Homo sapiens

<400> SEQUENCE: 2

```
Met Lys Phe Ile Ser Thr Ser Leu Leu Leu Met Leu Leu Val Ser Ser
  1               5                  10                  15

Leu Ser Pro Val Gln Gly Val Leu Glu Val Tyr Tyr Thr Ser Leu Arg
             20                  25                  30

Cys Arg Cys Val Gln Glu Ser Ser Val Phe Ile Pro Arg Arg Phe Ile
         35                  40                  45

Asp Arg Ile Gln Ile Leu Pro Arg Gly Asn Gly Cys Pro Arg Lys Glu
     50                  55                  60

Ile Ile Val Trp Lys Lys Asn Lys Ser Ile Val Cys Val Asp Pro Gln
 65                  70                  75                  80

Ala Glu Trp Ile Gln Arg Met Met Glu Val Leu Arg Lys Arg Ser Ser
                 85                  90                  95

Ser Thr Leu Pro Val Pro Val Phe Lys Arg Lys Ile Pro
            100                 105
```

<210> SEQ ID NO 3
<211> LENGTH: 1162
<212> TYPE: DNA
<213> ORGANISM: Mus musculus
<220> FEATURE:
<221> NAME/KEY: CDS
<222> LOCATION: (33)...(362)

<400> SEQUENCE: 3

```
gagctaaagg ttgaactcca cctccaggca ga atg agg ctc agc aca gca acg       53
                                   Met Arg Leu Ser Thr Ala Thr
                                     1               5 ctg ctt ctc ctc ctg gcc agc tgc ctc tct cca ggc cac ggt att ctg      101
Leu Leu Leu Leu Leu Ala Ser Cys Leu Ser Pro Gly His Gly Ile Leu
             10                  15                  20 gaa gcc cat tac aca aac tta aaa tgt agg tgt tct gga gtg att tca      149
Glu Ala His Tyr Thr Asn Leu Lys Cys Arg Cys Ser Gly Val Ile Ser
         25                  30                  35 act gtt gtc ggt cta aac atc ata gat cgg att caa gtt acg ccc cct      197
Thr Val Val Gly Leu Asn Ile Ile Asp Arg Ile Gln Val Thr Pro Pro
 40                  45                  50                  55 ggg aat ggc tgc ccc aaa act gaa gtt gtg atc tgg acc aag atg aag      245
Gly Asn Gly Cys Pro Lys Thr Glu Val Val Ile Trp Thr Lys Met Lys
                 60                  65                  70 aaa gtt ata tgt gtg aat cct cgt gcc aaa tgg tta caa aga tta tta      293
Lys Val Ile Cys Val Asn Pro Arg Ala Lys Trp Leu Gln Arg Leu Leu
             75                  80                  85 aga cat gtc caa agc aaa agt ctg tct tca act ccc caa gct cca gtg      341
Arg His Val Gln Ser Lys Ser Leu Ser Ser Thr Pro Gln Ala Pro Val
         90                  95                 100 agt aag aga aga gct gcc tga agccactatc atctcaaaag acacacctgc         392
Ser Lys Arg Arg Ala Ala
            105
```

-continued

```
accttttttt ttatccctgc tctgaatttt agatatgttc ttagttaaag aatttccaag    452
aaaataactc ccctctacaa acaaacatga ctgtaggtaa acaaagcaa aaacaaacaa     512 gcaaacaaac aaactaaaaa aaacccaatc ctgcaggagc tgagagggaa tgctcaagct    572
ccgttgcata cccaacccac atccttgttc cttaagaaag ctatttgag aacaggcatt     632 tagtgacaac ccacttcaga tgcatgtggt aatagatctg ttgtttaatg ttaaactatc    692
ctagattgtc gaggaatgaa aaacctacat gtcaaatgtg aacttgtagc tcgtactaac    752
aagaggtttg cgagatggac ttcagttatt ttgcacccct gtaaaacgca ggcttccaaa    812
atagtctcca gaaggttcct gggaagctgg tgcaatgcca tcatgaggtg gtgcaaagca    872
ggtctccttt agagaaaagc ttcctggggg aaacagtcct actttgaaag gttgcttgta    932
taagatttat tgtcttgcat taaaaccagt aacaattgaa agatcctcag cttaaaggtc    992
caggctcttc agcagtatac aaatatattc ctttgcactg tgaccctgat gatctatttt   1052
tattattcat atctttcaca cagacaaaat accagcctct tgtatcagat tctttaatgt   1112
ttcctattca tctggtgtca ttcaataaat gtaatcaaat gttttgctta              1162
```

<210> SEQ ID NO 4
<211> LENGTH: 109
<212> TYPE: PRT
<213> ORGANISM: Mus musculus

<400> SEQUENCE: 4

Met Arg Leu Ser Thr Ala Thr Leu Leu Leu Leu Ala Ser Cys Leu
1               5                   10                  15

Ser Pro Gly His Gly Ile Leu Glu Ala His Tyr Thr Asn Leu Lys Cys
                20                  25                  30

Arg Cys Ser Gly Val Ile Ser Thr Val Val Gly Leu Asn Ile Ile Asp
            35                  40                  45

Arg Ile Gln Val Thr Pro Pro Gly Asn Gly Cys Pro Lys Thr Glu Val
        50                  55                  60

Val Ile Trp Thr Lys Met Lys Lys Val Ile Cys Val Asn Pro Arg Ala
65                  70                  75                  80

Lys Trp Leu Gln Arg Leu Leu Arg His Val Gln Ser Lys Ser Leu Ser
                85                  90                  95

Ser Thr Pro Gln Ala Pro Val Ser Lys Arg Arg Ala Ala
            100                 105

<210> SEQ ID NO 5
<211> LENGTH: 82
<212> TYPE: PRT
<213> ORGANISM: Macaca fascicularis

<400> SEQUENCE: 5

Val Leu Glu Val Tyr Tyr Thr His Leu Arg Cys Arg Cys Val Gln Glu
1               5                   10                  15

Ser Ser Val Phe Ile Pro Arg Arg Phe Ile Asp Arg Ile Gln Ile Ser
                20                  25                  30

Pro Arg Gly Asn Gly Cys Pro Arg Lys Glu Ile Ile Val Trp Lys Lys
            35                  40                  45

Asn Lys Ser Val Val Cys Val Asp Pro Gln Ala Glu Trp Ile Gln Arg
        50                  55                  60

Ile Met Glu Met Leu Arg Lys Lys Ser Ser Thr Pro Pro Val Pro
65                  70                  75                  80

Val Phe

<210> SEQ ID NO 6
<211> LENGTH: 2902
<212> TYPE: DNA
<213> ORGANISM: Homo sapiens
<220> FEATURE:
<221> NAME/KEY: CDS
<222> LOCATION: (177)...(1295)

<400> SEQUENCE: 6

```
aaaaaaaaaa agtgatgagt tgtgaggcag gtcgcggccc tactgcctca ggagacgatg      60
cgcagctcat ttgcttaaat ttgcagctga cggctgccac ctctctagag gcacctggcg     120
gggagcctct caacataaga cagtgaccag tctggtgact cacagccggc acagcc atg     179
                                                               Met
                                                                 1 aac tac ccg cta acg ctg gaa atg gac ctc gag aac ctg gag gac ctg       227
Asn Tyr Pro Leu Thr Leu Glu Met Asp Leu Glu Asn Leu Glu Asp Leu
          5                   10                  15 ttc tgg gaa ctg gac aga ttg gac aac tat aac gac acc tcc ctg gtg       275
Phe Trp Glu Leu Asp Arg Leu Asp Asn Tyr Asn Asp Thr Ser Leu Val
         20                  25                  30 gaa aat cat ctc tgc cct gcc aca gag ggg ccc ctc atg gcc tcc ttc       323
Glu Asn His Leu Cys Pro Ala Thr Glu Gly Pro Leu Met Ala Ser Phe
     35                  40                  45 aag gcc gtg ttc gtg ccc gtg gcc tac agc ctc atc ttc ctc ctg ggc       371
Lys Ala Val Phe Val Pro Val Ala Tyr Ser Leu Ile Phe Leu Leu Gly
 50                  55                  60                  65 gtg atc ggc aac gtc ctg gtg ctg gtg atc ctg gag cgg cac cgg cag       419
Val Ile Gly Asn Val Leu Val Leu Val Ile Leu Glu Arg His Arg Gln
                 70                  75                  80 aca cgc agt tcc acg gag acc ttc ctg ttc cac ctg gcc gtg gcc gac       467
Thr Arg Ser Ser Thr Glu Thr Phe Leu Phe His Leu Ala Val Ala Asp
             85                  90                  95 ctc ctg ctg gtc ttc atc ttg ccc ttt gcc gtg gcc gag ggc tct gtg       515
Leu Leu Leu Val Phe Ile Leu Pro Phe Ala Val Ala Glu Gly Ser Val
        100                 105                 110 ggc tgg gtc ctg ggg acc ttc ctc tgc aaa act gtg att gcc ctg cac       563
Gly Trp Val Leu Gly Thr Phe Leu Cys Lys Thr Val Ile Ala Leu His
115                 120                 125 aaa gtc aac ttc tac tgc agc agc ctg ctc ctg gcc tgc atc gcc gtg       611
Lys Val Asn Phe Tyr Cys Ser Ser Leu Leu Leu Ala Cys Ile Ala Val
130                 135                 140                 145 gac cgc tac ctg gcc att gtc cac gcc gtc cat gcc tac cgc cac cgc       659
Asp Arg Tyr Leu Ala Ile Val His Ala Val His Ala Tyr Arg His Arg
                150                 155                 160 cgc ctc ctc tcc atc cac atc acc tgt ggg acc atc tgg ctg gtg ggc       707
Arg Leu Leu Ser Ile His Ile Thr Cys Gly Thr Ile Trp Leu Val Gly
            165                 170                 175 ttc ctc ctt gcc ttg cca gag att ctc ttc gcc aaa gtc agc caa ggc       755
Phe Leu Leu Ala Leu Pro Glu Ile Leu Phe Ala Lys Val Ser Gln Gly
        180                 185                 190 cat cac aac aac tcc ctg cca cgt tgc acc ttc tcc caa gag aac caa       803
His His Asn Asn Ser Leu Pro Arg Cys Thr Phe Ser Gln Glu Asn Gln
195                 200                 205 gca gaa acg cat gcc tgg ttc acc tcc cga ttc ctc tac cat gtg gcg       851
Ala Glu Thr His Ala Trp Phe Thr Ser Arg Phe Leu Tyr His Val Ala
210                 215                 220                 225 gga ttc ctg ctg ccc atg ctg gtg atg ggc tgg tgc tac gtg ggg gta       899
Gly Phe Leu Leu Pro Met Leu Val Met Gly Trp Cys Tyr Val Gly Val
```

-continued

|                                                                                                                                                  |      |
|--------------------------------------------------------------------------------------------------------------------------------------------------|------|
| gtg cac agg ttg cgc cag gcc cag cgg cgc cct cag cgg cag aag gca<br>Val His Arg Leu Arg Gln Ala Gln Arg Arg Pro Gln Arg Gln Lys Ala<br>245         250         255 | 947  |
| gtc agg gtg gcc atc ctg gtg aca agc atc ttc ttc ctc tgc tgg tca<br>Val Arg Val Ala Ile Leu Val Thr Ser Ile Phe Phe Leu Cys Trp Ser<br>260         265         270 | 995  |
| ccc tac cac atc gtc atc ttc ctg gac acc ctg gcg agg ctg aag gcc<br>Pro Tyr His Ile Val Ile Phe Leu Asp Thr Leu Ala Arg Leu Lys Ala<br>275         280         285 | 1043 |
| gtg gac aat acc tgc aag ctg aat ggc tct ctc ccc gtg gcc atc acc<br>Val Asp Asn Thr Cys Lys Leu Asn Gly Ser Leu Pro Val Ala Ile Thr<br>290         295         300         305 | 1091 |
| atg tgt gag ttc ctg ggc ctg gcc cac tgc tgc ctc aac ccc atg ctc<br>Met Cys Glu Phe Leu Gly Leu Ala His Cys Cys Leu Asn Pro Met Leu<br>310         315         320 | 1139 |
| tac act ttc gcc ggc gtg aag ttc cgc agt gac ctg tcg cgg ctc ctg<br>Tyr Thr Phe Ala Gly Val Lys Phe Arg Ser Asp Leu Ser Arg Leu Leu<br>325         330         335 | 1187 |
| acg aag ctg ggc tgt acc ggc cct gcc tcc ctg tgc cag ctc ttc cct<br>Thr Lys Leu Gly Cys Thr Gly Pro Ala Ser Leu Cys Gln Leu Phe Pro<br>340         345         350 | 1235 |
| agc tgg cgc agg agc agt ctc tct gag tca gag aat gcc acc tct ctc<br>Ser Trp Arg Arg Ser Ser Leu Ser Glu Ser Glu Asn Ala Thr Ser Leu<br>355         360         365 | 1283 |
| acc acg ttc tag gtcccagtgt ccccttttat tgctgctttt ccttggggca<br>Thr Thr Phe<br>370                                                                | 1335 |
| ggcagtgatg ctggatgctc cttccaacag gagctgggat cctaagggct caccgtggct                                                                                | 1395 |
| aagagtgtcc taggagtatc ctcatttggg gtagctagag gaaccaaccc ccatttctag                                                                                | 1455 |
| aacatccctg ccagctcttc tgccggccct ggggctaggc tggagcccag ggagcggaaa                                                                                | 1515 |
| gcagctcaaa ggcacagtga aggctgtcct tacccatctg cacccccctg ggctgagaga                                                                                | 1575 |
| acctcacgca cctcccatcc taatcatcca atgctcaaga aacaacttct acttctgccc                                                                                | 1635 |
| ttgccaacgg agagcgcctg cccctcccag aacacactcc atcagcttag gggctgctga                                                                                | 1695 |
| cctccacagc ttcccctctc tcctcctgcc cacctgtcaa acaaagccag aagctgagca                                                                                | 1755 |
| ccaggggatg agtggaggtt aaggctgagg aaaggccagc tggcagcaga gtgtggcctt                                                                                | 1815 |
| cggacaactc agtccctaaa aacacagaca ttctgccagg cccccaagcc tgcagtcatc                                                                                | 1875 |
| ttgaccaagc aggaagctca gactggttga gttcaggtag ctgcccctgg ctctgaccga                                                                                | 1935 |
| aacagcgctg ggtccacccc atgtcaccgg atcctgggtg gtctgcaggc agggctgact                                                                                | 1995 |
| ctaggtgccc ttggaggcca gccagtgacc tgaggaagcg tgaaggccga gaagcaagaa                                                                                | 2055 |
| agaaacccga cagagggaag aaaagagctt tcttcccgaa ccccaaggag ggagatggat                                                                                | 2115 |
| caatcaaacc cggcggtccc ctccgccagg cgagatgggg tggggtggag aactcctagg                                                                                | 2175 |
| gtggctgggt ccaggggatg ggaggttgtg ggcattgatg gggaaggagg ctggcttgtc                                                                                | 2235 |
| ccctcctcac tcccttccca taagctatag acccgaggaa actcagagtc ggaacggaga                                                                                | 2295 |
| aaggtggact ggaaggggcc cgtgggagtc atctcaacca tcccctccgt ggcatcacct                                                                                | 2355 |
| taggcaggga agtgtaagaa acacactgag gcagggaagt cccaggcccc caggaagccg                                                                                | 2415 |
| tgccctgccc ccgtgaggat gtcactcaga tggaaccgca ggaagctgct ccgtgcttgt                                                                                | 2475 |
| ttgctcacct ggggtgtggg aggcccgtcc ggcagtctg ggtgctccct accacctccc                                                                                 | 2535 |
| cagcctttga tcaggtgggg agtcagggac ccctgcccct gtcccactca agccaagcag                                                                                | 2595 |

```
ccaagctcct tgggaggccc cactggggaa ataacagctg tggctcacgt gagagtgtct    2655
tcacggcagg acaacgagga agccctaaga cgtccctttt ttctctgagt atctcctcgc    2715
aagctgggta atcgatgggg gagtctgaag cagatgcaaa gaggcaagag gctggatttt    2775
gaattttctt tttaataaaa aggcacctat aaaacaggtc aatacagtac aggcagcaca    2835 gagaccccg gaacaagcct aaaaattgtt tcaaaataaa aaccaagaag atgtcttcac     2895
atattgt                                                              2902
```

<210> SEQ ID NO 7
<211> LENGTH: 372
<212> TYPE: PRT
<213> ORGANISM: Homo sapiens

<400> SEQUENCE: 7

```
Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
        275                 280                 285

Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
```

```
305                 310                 315                 320
Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
                340                 345                 350

Pro Ser Trp Arg Arg Ser Ser Leu Ser Glu Ser Glu Asn Ala Thr Ser
                355                 360                 365

Leu Thr Thr Phe
        370

<210> SEQ ID NO 8
<211> LENGTH: 2614
<212> TYPE: DNA
<213> ORGANISM: Mus musculus
<220> FEATURE:
<221> NAME/KEY: CDS
<222> LOCATION: (44)...(1168)

<400> SEQUENCE: 8
cgacatcaga cagtgaccag cctggtgacg cagagctgca gct atg aac tac cca         55
                                                Met Asn Tyr Pro
                                                  1 cta acc ctg gac atg ggc tcc atc aca tac aat atg gat gac ctg tac        103
Leu Thr Leu Asp Met Gly Ser Ile Thr Tyr Asn Met Asp Asp Leu Tyr
 5                  10                  15                  20 aag gaa ctg gcc ttc tac agt aac agc acg gag att ccc cta cag gac        151
Lys Glu Leu Ala Phe Tyr Ser Asn Ser Thr Glu Ile Pro Leu Gln Asp
                 25                  30                  35 agt aac ttc tgc tct aca gtc gag gga ccc tta ctg acg tcc ttt aag        199
Ser Asn Phe Cys Ser Thr Val Glu Gly Pro Leu Leu Thr Ser Phe Lys
             40                  45                  50 gcg gta ttc atg cct gtg gcc tac agc ctc atc ttc ctc ctg ggt atg        247
Ala Val Phe Met Pro Val Ala Tyr Ser Leu Ile Phe Leu Leu Gly Met
         55                  60                  65 atg gga aac atc ctg gtg ctg gta atc ctg gag agg cac cgg cac act        295
Met Gly Asn Ile Leu Val Leu Val Ile Leu Glu Arg His Arg His Thr
 70                  75                  80 cgg agc tca acc gag acc ttc ctg ttc cac ctc gca gta gcc gac ctt        343
Arg Ser Ser Thr Glu Thr Phe Leu Phe His Leu Ala Val Ala Asp Leu
 85                  90                  95                 100 ctc tta gtc ttc atc ctg cct ttt gca gtg gct gag ggc tct gtg ggt        391
Leu Leu Val Phe Ile Leu Pro Phe Ala Val Ala Glu Gly Ser Val Gly
                105                 110                 115 tgg gtc cta ggg acc ttc ctc tgc aaa act gtg atc gct ctg cac aag        439
Trp Val Leu Gly Thr Phe Leu Cys Lys Thr Val Ile Ala Leu His Lys
            120                 125                 130 atc aat ttc tac tgc agc agc ctg ctg ctg gcc tgt ata gct gta gac        487
Ile Asn Phe Tyr Cys Ser Ser Leu Leu Leu Ala Cys Ile Ala Val Asp
        135                 140                 145 cgg tac cta gcc atc gtc cat gct gtt cac gcc tac cgc cgc cgt cga        535
Arg Tyr Leu Ala Ile Val His Ala Val His Ala Tyr Arg Arg Arg Arg
    150                 155                 160 ctc ctc tcc atc cac atc acc tgc acg gcc att tgg ctg gcc ggc ttc        583
Leu Leu Ser Ile His Ile Thr Cys Thr Ala Ile Trp Leu Ala Gly Phe
165                 170                 175                 180 ctg ttc gcc tta ccg gaa ctc ctc ttt gcc aag gtt ggc caa cct cat        631
Leu Phe Ala Leu Pro Glu Leu Leu Phe Ala Lys Val Gly Gln Pro His
                185                 190                 195 aac aac gac tcc tta cca cag tgc acc ttc tcc cag gaa aac gaa gcg        679
Asn Asn Asp Ser Leu Pro Gln Cys Thr Phe Ser Gln Glu Asn Glu Ala
```

-continued

```
                 200                 205                 210
gaa act aga gcc tgg ttc acc tcc cgt ttc ctc tac cac atc ggg ggc      727
Glu Thr Arg Ala Trp Phe Thr Ser Arg Phe Leu Tyr His Ile Gly Gly
        215                 220                 225 ttc cta cta ccg atg ctt gtg atg gga tgg tgt tac gtg ggc gtg gtc      775
Phe Leu Leu Pro Met Leu Val Met Gly Trp Cys Tyr Val Gly Val Val
    230                 235                 240 cac agg cta ctg cag gcc cag cgg cgc cct cag cgg cag aag gcg gtc      823
His Arg Leu Leu Gln Ala Gln Arg Arg Pro Gln Arg Gln Lys Ala Val
245                 250                 255                 260 agg gtg gcc att tta gtg aca agc att ttc ttc ctc tgc tgg tcg ccc      871
Arg Val Ala Ile Leu Val Thr Ser Ile Phe Phe Leu Cys Trp Ser Pro
                265                 270                 275 tac cac att gtc atc ttc cta gat aca ctg gag agg ctg aag gct gtg      919
Tyr His Ile Val Ile Phe Leu Asp Thr Leu Glu Arg Leu Lys Ala Val
            280                 285                 290 aat agc agc tgc gag ctg agt ggc tat ctc tct gtg gcc atc acc ttg      967
Asn Ser Ser Cys Glu Leu Ser Gly Tyr Leu Ser Val Ala Ile Thr Leu
        295                 300                 305 tgt gaa ttc ctg ggc ctg gca cac tgc tgt ctc aat ccc atg ctc tac     1015
Cys Glu Phe Leu Gly Leu Ala His Cys Cys Leu Asn Pro Met Leu Tyr
    310                 315                 320 acc ttc gct ggc gta aag ttc cgc agt gac ctc tct cgg ctt ctg acc     1063
Thr Phe Ala Gly Val Lys Phe Arg Ser Asp Leu Ser Arg Leu Leu Thr
325                 330                 335                 340 aag ctg ggc tgt gct ggc ccg gcc tcc ctt tgc caa ctt ttc ccc aac     1111
Lys Leu Gly Cys Ala Gly Pro Ala Ser Leu Cys Gln Leu Phe Pro Asn
                345                 350                 355 tgg cgc aag agt agt ctc tct gag tca gag aat gct act tcc ctc acc     1159
Trp Arg Lys Ser Ser Leu Ser Glu Ser Glu Asn Ala Thr Ser Leu Thr
            360                 365                 370 acc ttc tag atcccggaag tctcggggcc cctgtctgtt tctgttttcc             1208
Thr Phe ttgggaggat aaagtggtgg cggaacccat ccaactcgag cttgggccag tgtccccaga    1268
tgggaaagct agataaactc tctcaaactt tcccaaaggg gaaagcagcc caaaggcaaa    1328
gcaagctata tccaggccac ctgtatcacc ttagatgaag agaactccat acacctccca    1388
tcctaaccag ctaaagctaa gctcagcttt atttcttcct ggccataggg acaaccacct    1448
ctgctgtggc ccacagtctc atcttcctcc tgattatgag cccagactct cctcccagaa    1508
tgtattccat catcttaaag actactggct gccacagcta cccaccactc ctataccaca    1568
gaggaatagc cagctggcgg cggcagacta tggccttaat gtgcctgtct cataaataca    1628
gacttcatgc cagaccttca accgtgcctt tctcttaacc aagcagaaag ctgaaaccga    1688
tctactttag gtagctgtct ggttccaacc taaccagcat tgggtcagcc ccatgttact    1748
ggatcttgga ttacagactg agggcaagtt ccagaaggtt ctggaagcta gccagtatcc    1808
taagaagagt aaagggcaag ccagcaggaa agagcccag tggaaaagtg aaagacacc     1868 ttttccaggc tctaaggaag aacaagtaaa aatcaaaccc agctgtcttc tccacccaat    1928
gtaccaaagc ttacgactg gtggggaaat gagatccagg gccctcgtgg attctacgca    1988
ccaatgggaa aggaagccaa cttgcctggg gaaagcaaga tagcaaagtg gtcctagcct    2048
cgagagaggg gacacctagc taagagaatg acgacagagg ttcctgtctt cattaggcag    2108
aggcaatata agaagccaac ctgggcaggc aagtcctcaa accccaggaa ggcagtaccc    2168
tgcccctggg agggtaccac tcacatggaa ccagaggaag ctgctccatg catacatagg    2228
```

```
ggaagttagc aggcaattct gagctcggct tcctcccagc caccgatctg ggggcgtggg    2288
ggtaggaagc agagttgcct agtaccactc aagccaaccg tacaagctcc ctggggatc    2348 ccactgggga aaccaatgct atagcttcag agactgtatc ctcattgcag aaccgtgaag    2408
acacctgggg acccccttt ctgctcccag catccaacaa ccagctggga agaggcaaac    2468
cgggcacaga aataaaaatg caagagatgg cattttttgaa ttttctcttt ttaataaaaa    2528
ggcacctata aaacaggtca atacaggcag agacccccgg aacaagccta aaaagtgttt    2588
caaaataaaa acaggaagat gtcttc                                          2614

<210> SEQ ID NO 9
<211> LENGTH: 374
<212> TYPE: PRT
<213> ORGANISM: Mus musculus

<400> SEQUENCE: 9

Met Asn Tyr Pro Leu Thr Leu Asp Met Gly Ser Ile Thr Tyr Asn Met
  1               5                  10                  15

Asp Asp Leu Tyr Lys Glu Leu Ala Phe Tyr Ser Asn Ser Thr Glu Ile
             20                  25                  30

Pro Leu Gln Asp Ser Asn Phe Cys Ser Thr Val Glu Gly Pro Leu Leu
         35                  40                  45

Thr Ser Phe Lys Ala Val Phe Met Pro Val Ala Tyr Ser Leu Ile Phe
     50                  55                  60

Leu Leu Gly Met Met Gly Asn Ile Leu Val Leu Val Ile Leu Glu Arg
 65                  70                  75                  80

His Arg His Thr Arg Ser Ser Thr Glu Thr Phe Leu Phe His Leu Ala
                 85                  90                  95

Val Ala Asp Leu Leu Leu Val Phe Ile Leu Pro Phe Ala Val Ala Glu
            100                 105                 110

Gly Ser Val Gly Trp Val Leu Gly Thr Phe Leu Cys Lys Thr Val Ile
        115                 120                 125

Ala Leu His Lys Ile Asn Phe Tyr Cys Ser Ser Leu Leu Leu Ala Cys
    130                 135                 140

Ile Ala Val Asp Arg Tyr Leu Ala Ile Val His Ala Val His Ala Tyr
145                 150                 155                 160

Arg Arg Arg Arg Leu Leu Ser Ile His Ile Thr Cys Thr Ala Ile Trp
                165                 170                 175

Leu Ala Gly Phe Leu Phe Ala Leu Pro Glu Leu Leu Phe Ala Lys Val
            180                 185                 190

Gly Gln Pro His Asn Asn Asp Ser Leu Pro Gln Cys Thr Phe Ser Gln
        195                 200                 205

Glu Asn Glu Ala Glu Thr Arg Ala Trp Phe Thr Ser Arg Phe Leu Tyr
    210                 215                 220

His Ile Gly Gly Phe Leu Leu Pro Met Leu Val Met Gly Trp Cys Tyr
225                 230                 235                 240

Val Gly Val Val His Arg Leu Leu Gln Ala Gln Arg Arg Pro Gln Arg
                245                 250                 255

Gln Lys Ala Val Arg Val Ala Ile Leu Val Thr Ser Ile Phe Phe Leu
            260                 265                 270

Cys Trp Ser Pro Tyr His Ile Val Ile Phe Leu Asp Thr Leu Glu Arg
        275                 280                 285

Leu Lys Ala Val Asn Ser Ser Cys Glu Leu Ser Gly Tyr Leu Ser Val
    290                 295                 300
```

Ala Ile Thr Leu Cys Glu Phe Leu Gly Leu Ala His Cys Cys Leu Asn
305                 310                 315                 320

Pro Met Leu Tyr Thr Phe Ala Gly Val Lys Phe Arg Ser Asp Leu Ser
                325                 330                 335

Arg Leu Leu Thr Lys Leu Gly Cys Ala Gly Pro Ala Ser Leu Cys Gln
                340                 345                 350

Leu Phe Pro Asn Trp Arg Lys Ser Ser Leu Ser Glu Ser Glu Asn Ala
            355                 360                 365

Thr Ser Leu Thr Thr Phe
    370

<210> SEQ ID NO 10
<211> LENGTH: 123
<212> TYPE: PRT
<213> ORGANISM: Artificial Sequence
<220> FEATURE:
<223> OTHER INFORMATION: H1609; VH domain of 3D2 antibody

<400> SEQUENCE: 10

Glu Val Gln Leu Gln Glu Ser Gly Pro Gly Ile Leu Gln Pro Ser Gln
1               5                   10                  15

Thr Leu Asn Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Arg Arg Tyr Asn Pro Ala
    50                  55                  60

Leu Lys Ser Arg Leu Thr Ile Ser Lys Glu Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Thr Arg Ile Ala Gly Tyr Tyr Gly Ser Arg Asp Trp Phe Ala Tyr
            100                 105                 110

Trp Gly Gln Gly Thr Thr Val Thr Val Ser Ser
            115                 120

<210> SEQ ID NO 11
<211> LENGTH: 7
<212> TYPE: PRT
<213> ORGANISM: Artificial Sequence
<220> FEATURE:
<223> OTHER INFORMATION: H1609-CDR1

<400> SEQUENCE: 11

Thr Phe Gly Met Gly Val Gly
1               5

<210> SEQ ID NO 12
<211> LENGTH: 16
<212> TYPE: PRT
<213> ORGANISM: Artificial Sequence
<220> FEATURE:
<223> OTHER INFORMATION: H1609-CDR2

<400> SEQUENCE: 12

His Ile Trp Trp Asp Asp Arg Arg Tyr Asn Pro Ala Leu Lys Ser
1               5                   10                  15

<210> SEQ ID NO 13
<211> LENGTH: 13
<212> TYPE: PRT

```
<213> ORGANISM: Artificial Sequence
<220> FEATURE:
<223> OTHER INFORMATION: H1609-CDR3

<400> SEQUENCE: 13

Ile Ala Gly Tyr Tyr Gly Ser Arg Asp Trp Phe Ala Tyr
1               5                   10

<210> SEQ ID NO 14
<211> LENGTH: 123
<212> TYPE: PRT
<213> ORGANISM: Artificial Sequence
<220> FEATURE:
<223> OTHER INFORMATION: H5188/H2177; VH domain from MAb 5378 and 5261

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Thr Phe
            20                  25                  30

Gly Met Gly Val Gly Trp Ile Arg Gln Pro Pro Gly Lys Gly Leu Glu
        35                  40                  45

Trp Ile Ala His Ile Trp Trp Asp Asp Arg Arg Tyr Asn Pro Ala
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ile Ala Gly Tyr Tyr Gly Ser Arg Asp Trp Phe Ala Tyr
            100                 105                 110

Trp Gly Gln Gly Thr Thr Val Thr Val Ser Ser
        115                 120

<210> SEQ ID NO 15
<211> LENGTH: 111
<212> TYPE: PRT
<213> ORGANISM: Artificial Sequence
<220> FEATURE:
<223> OTHER INFORMATION: L0293; VL domain from MAb 3D2

<400> SEQUENCE: 15

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met His Trp Tyr Gln Gln Lys Pro Gly Gln Pro Pro
        35                  40                  45

Lys Leu Leu Ile Phe Arg Ala Ser Asp Leu Glu Ser Gly Ile Pro Ala
    50                  55                  60

Arg Phe Ser Gly Ser Gly Ser Arg Thr Asp Phe Thr Leu Thr Val Asn
65                  70                  75                  80

Pro Val Glu Thr Asp Asp Val Ala Thr Tyr Phe Cys Gln Gln Ser Asn
                85                  90                  95

Lys Asp Pro Trp Thr Phe Gly Gly Gly Thr Lys Leu Glu Ile Lys
            100                 105                 110

<210> SEQ ID NO 16
<211> LENGTH: 15
<212> TYPE: PRT
<213> ORGANISM: Artificial Sequence
```

```
<220> FEATURE:
<223> OTHER INFORMATION: L0293-CDR1

<400> SEQUENCE: 16

Arg Ala Ser Glu Ser Val Asp Asn Ser Gly Ile Ser Phe Met His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: L0293-CDR2

<400> SEQUENCE: 17

Arg Ala Ser Asp Leu Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: L0293-CDR3

<400> SEQUENCE: 18

Gln Gln Ser Asn Lys Asp Pro Trp Thr
1               5

<210> SEQ ID NO 19
<211> LENGTH: 111
<212> TYPE: PRT
<213> ORGANISM: Artificial Sequence
<220> FEATURE:
<223> OTHER INFORMATION: L5153/L5140; VL domains from MAb 5378 and 5261

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Met
                20                  25                  30

Gly Ile Ser Phe Met His Trp Tyr Gln Gln Lys Pro Gly Lys Ala Pro
            35                  40                  45

Lys Leu Leu Ile Phe Arg Ala Ser Asp Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Lys Asp Pro Trp Thr Phe Gly Gln Gly Thr Lys Leu Glu Ile Lys
            100                 105                 110

<210> SEQ ID NO 20
<211> LENGTH: 15
<212> TYPE: PRT
<213> ORGANISM: Artificial Sequence
<220> FEATURE:
<223> OTHER INFORMATION: L5153-CDR1

<400> SEQUENCE: 20

Arg Ala Ser Glu Ser Val Asp Asn Met Gly Ile Ser Phe Met His
1               5                   10                  15
```

```
<210> SEQ ID NO 21
<211> LENGTH: 111
<212> TYPE: PRT
<213> ORGANISM: Artificial Sequence
<220> FEATURE:
<223> OTHER INFORMATION: L5055; VL domain of MAb 5080

<400> SEQUENCE: 21
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Ser
            20                  25                  30

Gly Ile Ser Phe Met His Trp Tyr Gln Gln Lys Pro Gly Lys Ala Pro
        35                  40                  45

Lys Leu Leu Ile Phe Arg Ala Ser Asp Leu Glu Ser Gly Val Pro Ser
    50                  55                  60

Gly Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Lys Asp Pro Trp Thr Phe Gly Gln Gly Thr Lys Leu Glu Ile Lys
            100                 105                 110

```
<210> SEQ ID NO 22
<211> LENGTH: 21
<212> TYPE: DNA
<213> ORGANISM: Artificial Sequence
<220> FEATURE:
<223> OTHER INFORMATION: H. suis 16S rRNA forward primer

<400> SEQUENCE: 22
ttgggaggct tgtctttcc a                                             21

<210> SEQ ID NO 23
<211> LENGTH: 21
<212> TYPE: DNA
<213> ORGANISM: Artificial Sequence
<220> FEATURE:
<223> OTHER INFORMATION: H. suis 16S rRNA reverse primer

<400> SEQUENCE: 23
gattagctct gcctcgcggc t                                            21

<210> SEQ ID NO 24
<211> LENGTH: 23
<212> TYPE: DNA
<213> ORGANISM: Artificial Sequence
<220> FEATURE:
<223> OTHER INFORMATION: TGF-beta sense primer

<400> SEQUENCE: 24
tcttggtcca gatcacaact tca                                          23

<210> SEQ ID NO 25
<211> LENGTH: 19
<212> TYPE: DNA
<213> ORGANISM: Artificial Sequence
<220> FEATURE:
<223> OTHER INFORMATION: TGF-beta antisense primer

<400> SEQUENCE: 25
cactgatacg cctgagtgr                                               19
```

```
<210> SEQ ID NO 26
<211> LENGTH: 18
<212> TYPE: DNA
<213> ORGANISM: Artificial Sequence
<220> FEATURE:
<223> OTHER INFORMATION: IL-6 sense primer

<400> SEQUENCE: 26
gtgagcgctg aatcgaaa                                                 18

<210> SEQ ID NO 27
<211> LENGTH: 23
<212> TYPE: DNA
<213> ORGANISM: Artificial Sequence
<220> FEATURE:
<223> OTHER INFORMATION: IL-6 antisense primer

<400> SEQUENCE: 27
gaggatacca ctcccaacag acc                                           23

<210> SEQ ID NO 28
<211> LENGTH: 20
<212> TYPE: DNA
<213> ORGANISM: Artificial Sequence
<220> FEATURE:
<223> OTHER INFORMATION: beta-actin sense primer

<400> SEQUENCE: 28
atcactgacg ctgattgcac                                               20

<210> SEQ ID NO 29
<211> LENGTH: 20
<212> TYPE: DNA
<213> ORGANISM: Artificial Sequence
<220> FEATURE:
<223> OTHER INFORMATION: beta-actin antisense primer

<400> SEQUENCE: 29
aaggccaacc gtgaaaagat                                               20
```